(12) United States Patent
Pandurangi

(10) Patent No.: US 11,957,732 B2
(45) Date of Patent: Apr. 16, 2024

(54) COMPOSITIONS AND METHODS FOR SENSITIZING LOW RESPONSIVE TUMORS TO CANCER THERAPY

(71) Applicant: Raghoottama Pandurangi, Saint Charles, MO (US)

(72) Inventor: Raghoottama Pandurangi, Saint Charles, MO (US)

(*) Notice: Subject to any disclaimer, the term of this patent is extended or adjusted under 35 U.S.C. 154(b) by 193 days.

(21) Appl. No.: 15/749,225

(22) PCT Filed: Dec. 23, 2016

(86) PCT No.: PCT/US2016/068554
§ 371 (c)(1),
(2) Date: Jan. 31, 2018

(87) PCT Pub. No.: WO2017/131911
PCT Pub. Date: Aug. 3, 2017

(65) Prior Publication Data
US 2018/0318388 A1 Nov. 8, 2018

Related U.S. Application Data

(60) Provisional application No. 62/287,221, filed on Jan. 26, 2016.

(51) Int. Cl.
| | | |
|---|---|---|
| A61K 31/555 | (2006.01) | |
| A61K 31/337 | (2006.01) | |
| A61K 31/355 | (2006.01) | |
| A61K 31/704 | (2006.01) | |
| A61K 38/17 | (2006.01) | |
| A61K 45/06 | (2006.01) | |
| A61K 47/60 | (2017.01) | |
| A61K 47/65 | (2017.01) | |
| G01N 33/574 | (2006.01) | |

(52) U.S. Cl.
CPC .......... *A61K 38/177* (2013.01); *A61K 31/337* (2013.01); *A61K 31/355* (2013.01); *A61K 31/555* (2013.01); *A61K 31/704* (2013.01); *A61K 38/1729* (2013.01); *A61K 45/06* (2013.01); *A61K 47/60* (2017.08); *A61K 47/65* (2017.08); *C07K 2319/00* (2013.01); *G01N 33/57415* (2013.01); *G01N 33/57446* (2013.01)

(58) Field of Classification Search
CPC .............. A61K 31/355; A61K 47/6803; A61K 47/551; A61K 47/55; A61K 45/06; A61K 2300/00; C07K 2319/00; C07K 2319/33; C07K 2319/74; C07K 2319/75; C07K 2319/715; C07K 16/18; C07K 16/28; A61P 35/00
See application file for complete search history.

(56) References Cited

U.S. PATENT DOCUMENTS

| | | | |
|---|---|---|---|
| 2003/0220313 A1* | 11/2003 | Ray | C07J 43/00 540/107 |
| 2010/0111866 A1* | 5/2010 | Kratz | A61K 47/643 424/9.1 |

OTHER PUBLICATIONS

Siegemund et al (Cell Death and Disease, 2012, vol. 3, pp. e295) (Year: 2012).*
Zhao et al (Journal of Medicinal Chemistry, 2007, vol. 50, pp. 4471-4481). (Year: 2007).*
Wang et al (Cancer Research, 2007, vol. 67, pp. 3337-3343) (Year: 2007).*
Wang et al (Molecular Nutrition and Food Research, 2006, vol. 50, pp. 675-685) (Year: 2006).*
SCiBX, 2013, 6(34). (Year: 2013).*
Raju et al (Expert Opinion on Drug Delivery, 2013, vol. 10, pp. 747-760) (Year: 2013).*
Junyaprasert et al (Colloids and Surfaces B: Biointerfaces, 2015, vol. 136, pp. 383-393) (Year: 2015).*
Kutty et al (Biomaterials, 2015, vol. 58-69). (Year: 2015).*
The abstract of Kumar et al (Journal of the American College of Nutrition, 2002, vol. 21, pp. 339-343) (Year: 2002).*
The abstract of Ng et al.(Breast Cancer Research and Treatment, 2001, vol. 69, No. 3, p. 303) (Year: 2001).*
Badran et al (International Journal of Oncology, 2010, vol. 36, pp. 1229-1234) (Year: 2010).*
Ethirajan et al (Chemical Society Review, 2011, vol. 40, pp. 340-362) (Year: 2011).*

(Continued)

*Primary Examiner* — Karen A. Canella
(74) *Attorney, Agent, or Firm* — Raghavan Rajagopalan

(57) ABSTRACT

The present invention discloses compositions and methods for selectively delivering apoptosis inducing agents to the tumor prior to conventional therapeutic treatment protocol. Specifically, the present invention relates to an ensemble (or 'AAAPT bioconjugate') comprising an

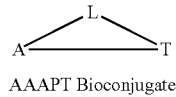

AAAPT Bioconjugate apoptogen (A) and a tumor targeting group (T), wherein the apoptogen is either connected directly to the targeting group or optionally attached through an intervening linker (L). The apoptogen may be a small or large molecule that activates apoptosis pathway and causes cell death. The targeting vector may be a small or large molecule that delivers the apoptogen selectively to the tumors. The linker may comprise simple alkylene chain or may contain functional groups that are capable of being cleaved by enzymatic process.

6 Claims, 28 Drawing Sheets
Specification includes a Sequence Listing.

(56) References Cited

OTHER PUBLICATIONS

Oleinick et al (Photochem Photobiol Sci, 2002, vol. 1, pp. 1-21) (Year: 2002).*
Susin et al (Nature, 1999, vol. 397, pp. 441-446) (Year: 1999).*
Kascakova et al (PLoS One, 2014, vol. 9, e104448) (Year: 2014).*
McLennan et al (Cardiovascular and Interventional Radiology, 2012, vol. 35, pp. 645-652) (Year: 2012).*
The abstract of Jayaram et al (Current Medicinal chemistry, 2002, vol. 9, pp. 787-792) (Year: 2002).*
Ryser and Shen (PNAS, 1978, vol. 75, pp. 3867-3870) (Year: 1978).*
Wang and Low (Journal of Controlled Release, 1998, vol. 53, pp. 39-48) i (Year: 1998).*
Leamon et al (The Journal of Biological Chemistry, 1993, vol. 268, pp. 24847-24854) (Year: 1993).*
Abstract of Wu et al (Progress in Physiology, 2014, vol. 45, No. 1, pp. 45-48) (Year: 2014).*
Hsiao et al (Agriculture and Food Chemistry, 2013, vol. 61, pp. 10063-10073) (Year: 2013).*
Lynn et al (Blood, 2015, vol. 125, pp. 3466-3476) (Year: 2015).*
Lowe et al (Advances in Protein Chemistry and Structural Biology, 2011, vol. 84, pp. 41-61) (Year: 2011).*
Spivak et al (Russian Chemical bulletin, 2010, vol. 59, pp. 241-250) (Year: 2010).*

* cited by examiner

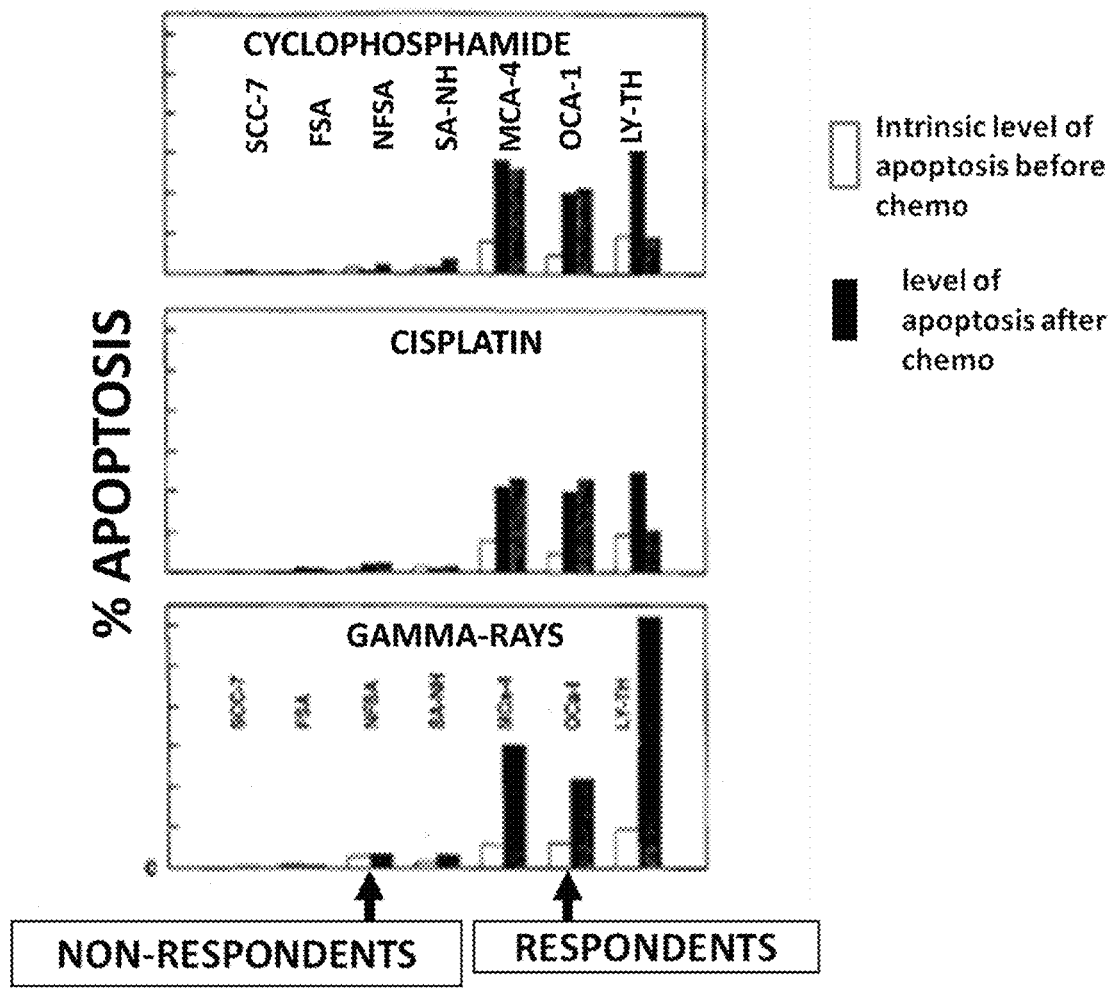
Figure 1: Apoptosis index correlated to response from anticancer agents.

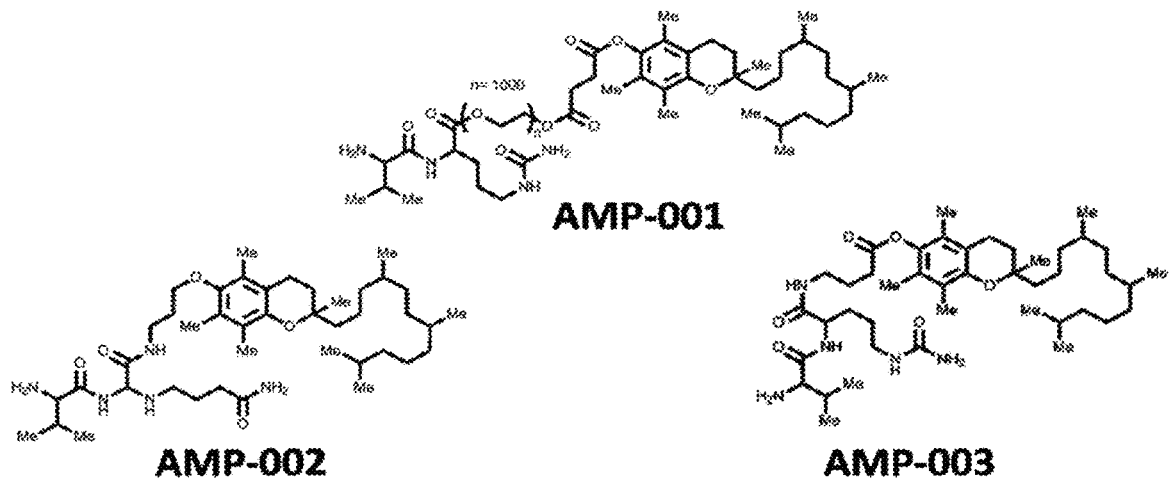

(SEQUENCE ID NO: 003)

Structure of AMP-004 (hBD-1, Human Beta Defensin

SEQ ID NO: 003

Xaa Glu Glu Glu Pro Xaa Gly Xaa Tyr Leu Asp His Tyr Asn Cys Val Ser Ser Gly Gly Gln Cys Leu
1          5                    10                   15                        20

Tyr Ser Ala Cys Pro Ile Phe Thr Lys Ile Gln Gly Thr Cys Tyr Arg Gly Lys Ala Lys Cys Cys Lys
       25                   30                   35                   40                        45

Disulfide bonds between cysteines: 15 and 44; 22 and 37; and 27 and 45). Position 1, Xaa = N-acetylglutamic acid; position 6, Xaa = citrulline; position 8, Xaa = homophenylalanine.

MMP-2 Cleavable Bond

Ac-E-E-E-E-P-Cit-G-Hof-Y-L------DHYNCVSSGGQCLYSACPIFTKIQGTCYRGKAKCCK

Figure. 2A: Structures of some embodiments of AAAPT and AAAPT bioconjugates, AMP-001 to AMP-004.

Structures of AMP-005, AMP-006 and AMP-007

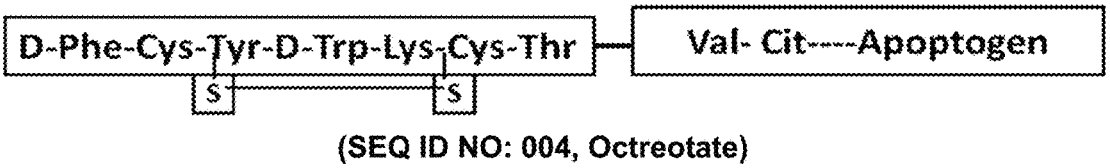

(SEQ ID NO: 004, Octreotate)

SEQ ID NO: 004

Xaa Cys Tyr Xaa Lys Cys Thr Val Xaa
 1         4

Position 1, Xaa = d-phenylalanine; position 4; Xaa = d-tryptophan; and position 9, Xaa = citrulline; disulfide bond between cysteines 2 and 6.

Structures of AMP-005, AMP-006 and AMP-007

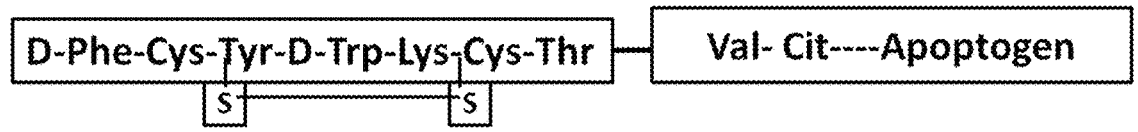

Apoptogens

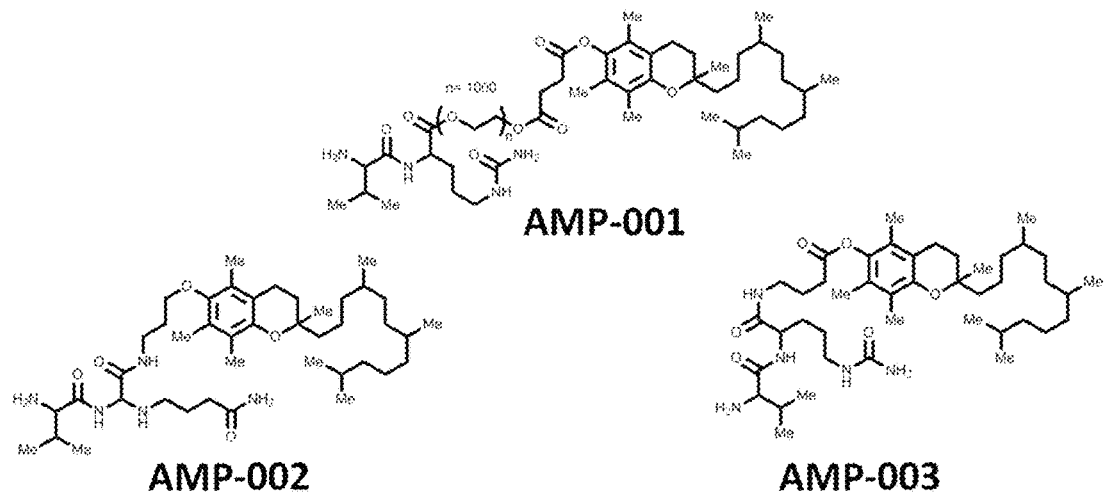

AMP-005: Octreotate + AMP-001, AMP-006: Octreotate + AMP-002, AMP-007: Octreotate + AMP-003

Figure 2B. Structures of some embodiment of AAAPT and AAAPT bioconjugates, AMP-005 to AMP-007.

AMP-008
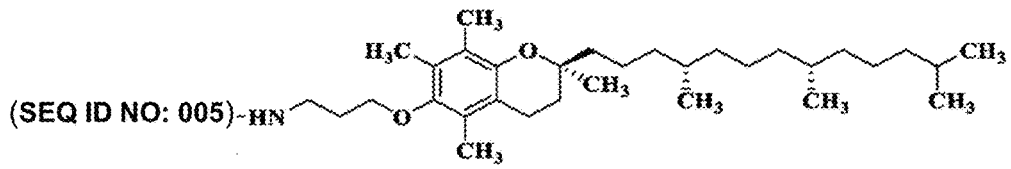
SEQ ID NO: 005
Cys Tyr Val Gln Arg Lyr Arg Gln Arg Leu Met Pro Cys
1           5                       10
Disulfide linkage between cysteines 1 and 13.
AMP-009
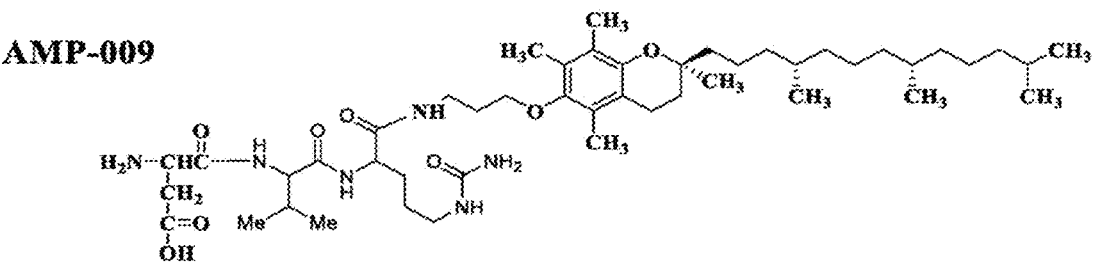
AMP-010
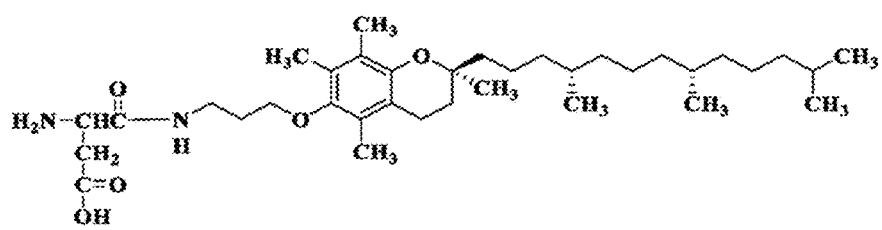
AMP-011
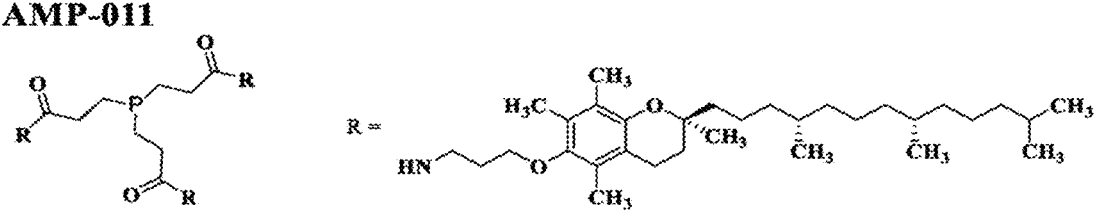
AMP-012
SEQ ID NO: 009
Xaa Val Val Xaa
1           4
Positions 1 and 4, Xaa = citrulline;
Figure 2C. Structures of some embodiment of AAAPT and AAAPT bioconjugates, AMP-008 to AMP-012.

AMP-013
(SEQ ID NO: 006)
(SEQ ID NO: 006)
SEQ ID NO: 006
Cys Arg Gly Phe Arg Arg Arg Cys Arg
1               5
Disulfide linkage between cysteines 1 and 8.
AMP-014
(SEQ ID NO: 007)-
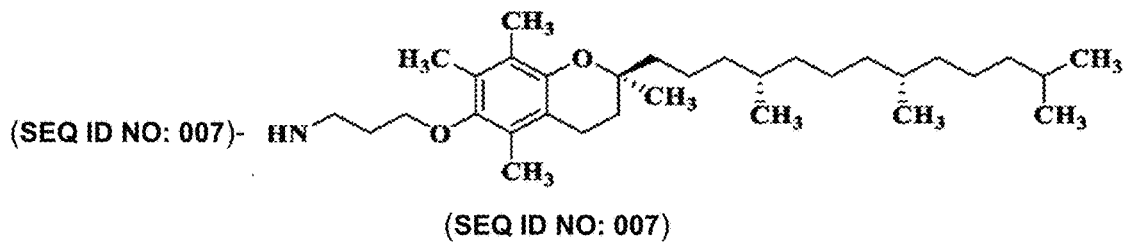
(SEQ ID NO: 007)
SEQ ID NO: 007
Cys Ile Phe Leu Leu Trp Gln Arg Cys Val Xaa Arg
1               5                   10
Position 11, Xaa = Citrulline. Disulfide linkage between cysteines 1 and 9.
AMP-015
COOH-PEG13-R
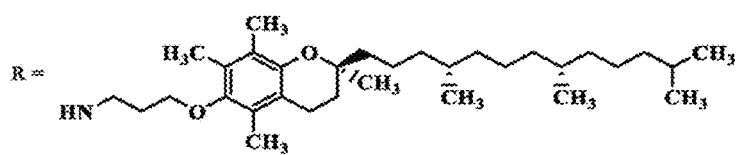
AMP-016
COOH-PEG13-R2
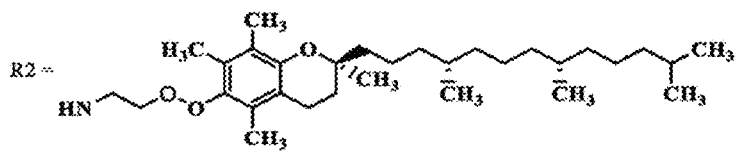
Figure 2D. Structures of some embodiment of AAAPT and AAAPT bioconjugates, AMP-013 to AMP-016.

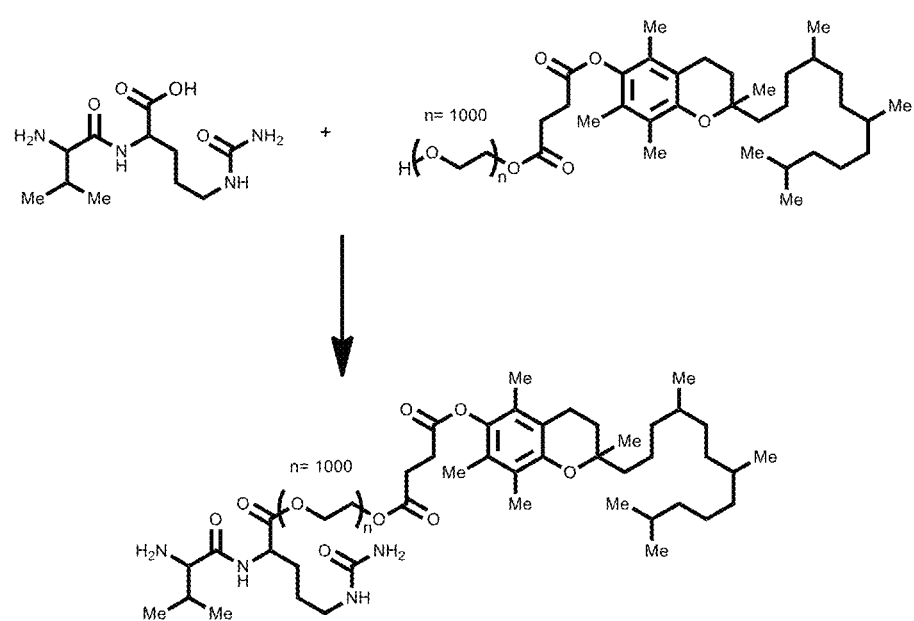
Figure 3A: General synthetic scheme for the preparation of AAAPT AMP-001.

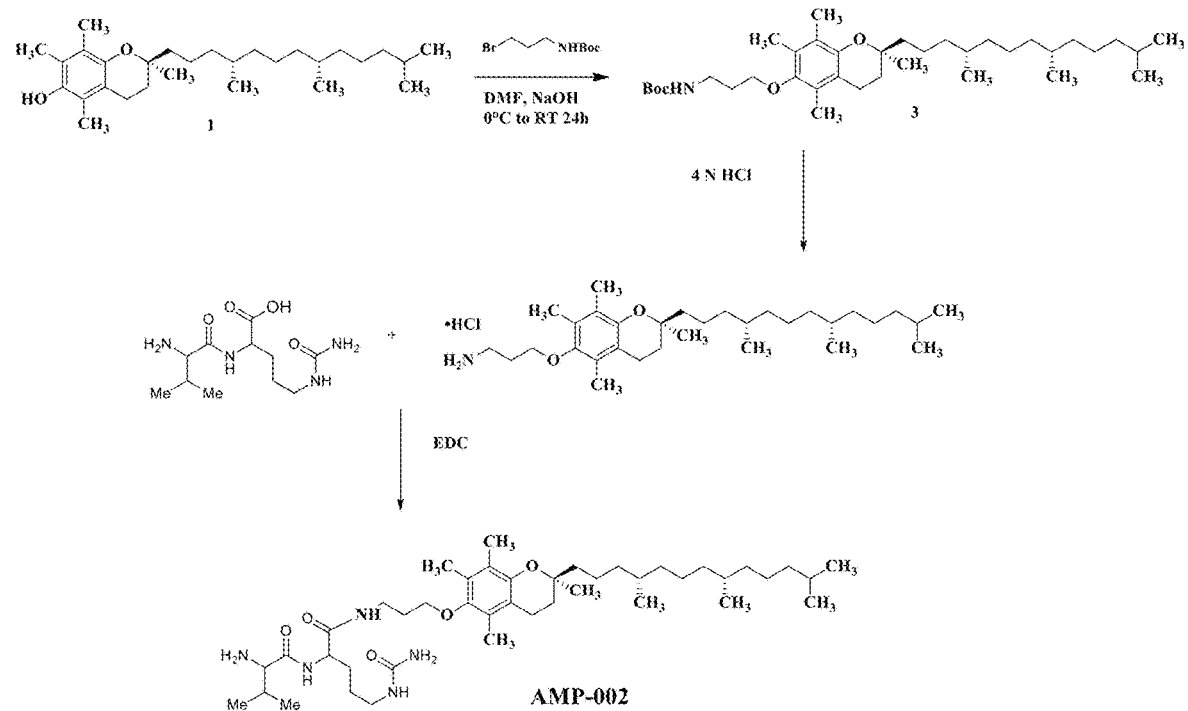
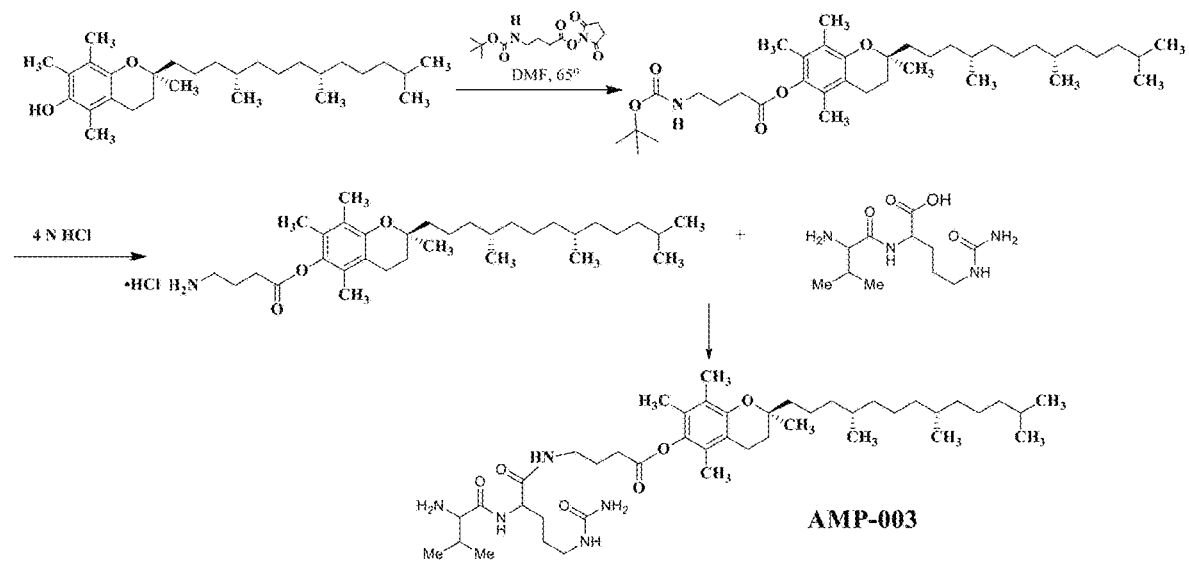
Figure 3B. General synthetic scheme for the preparation of AAAPT AMP-002 and AMP-003.

AMP-004: MMP-2 Cleavable Peptide Sequence ID No. 002; β-Defensin Peptide Sequence ID No. 001
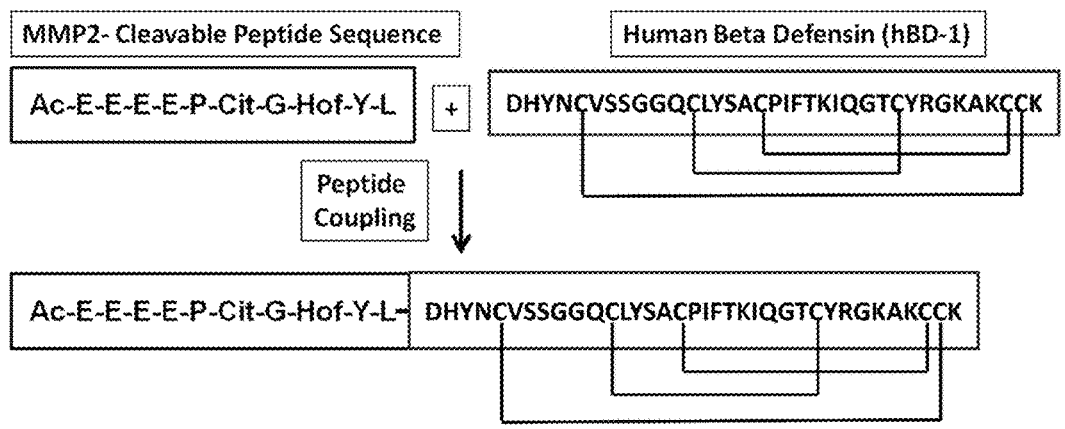
AMP-005, AMP-006 and AMP-007: Octreotate Sequence ID No. 004
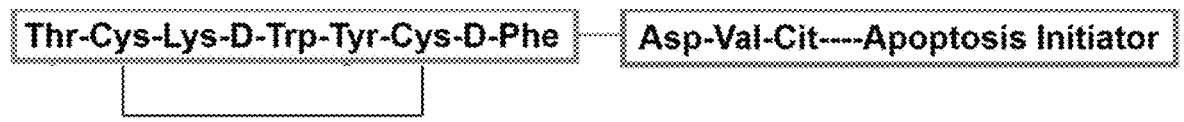
Figure 3C: General synthetic scheme for the preparation of AAAPT bioconjugates, AMP-004 to AMP-007.

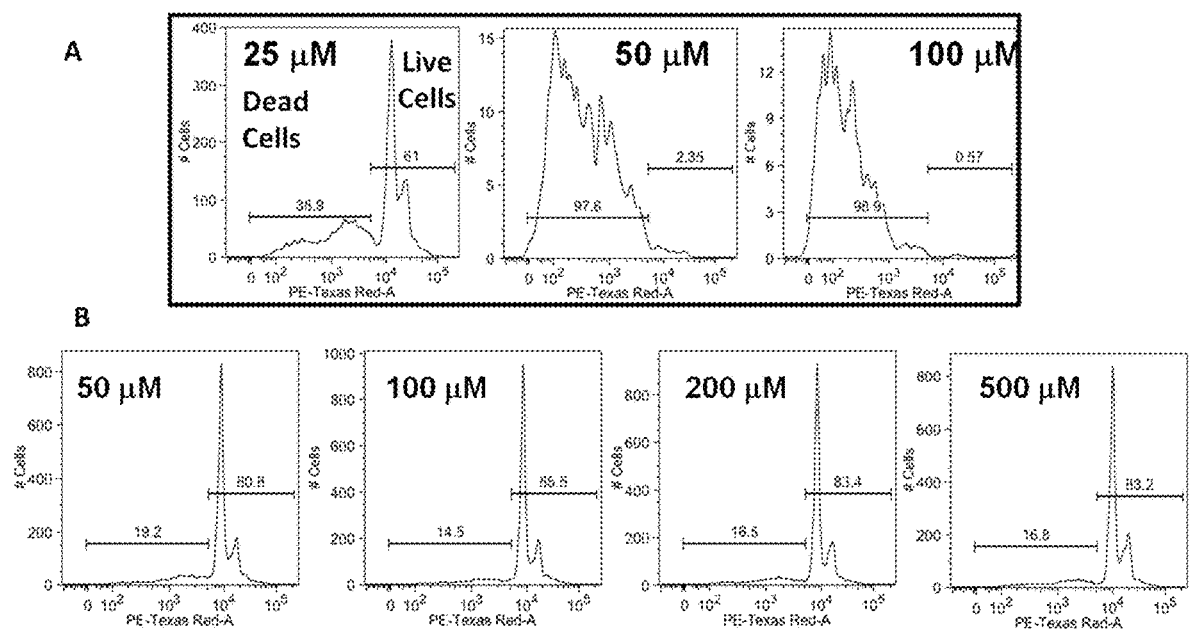
Figure 4. Cancer cell death induction by AMP-001.

A
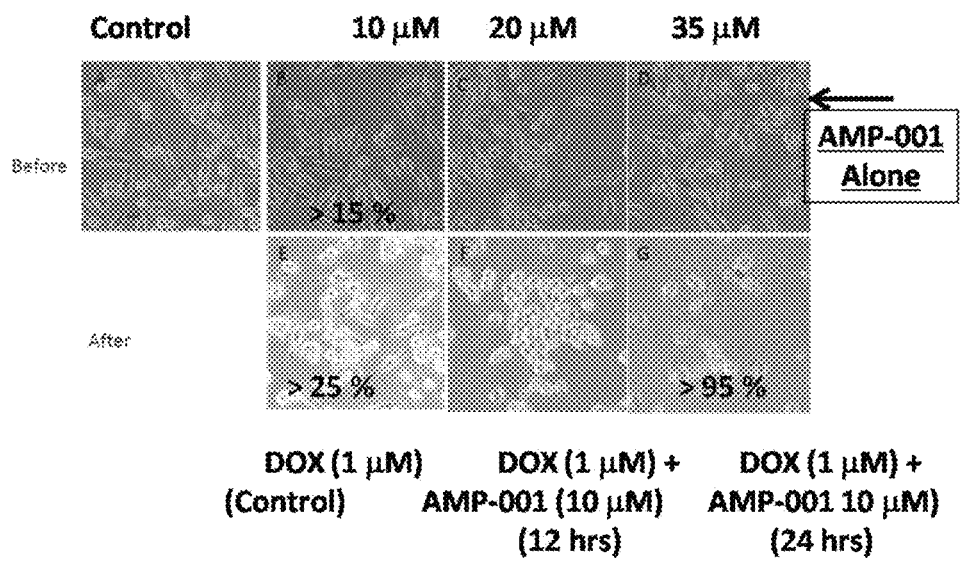
B: Synergy with doxorubicin on tumor cells derived from patient cells.
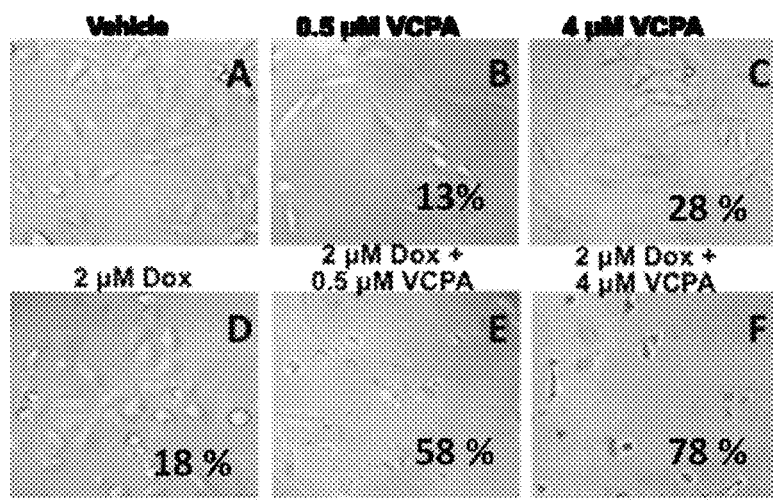
Figure 5. Synergistic cell death effect of AMP-001 and doxorubicin on cancer cells.

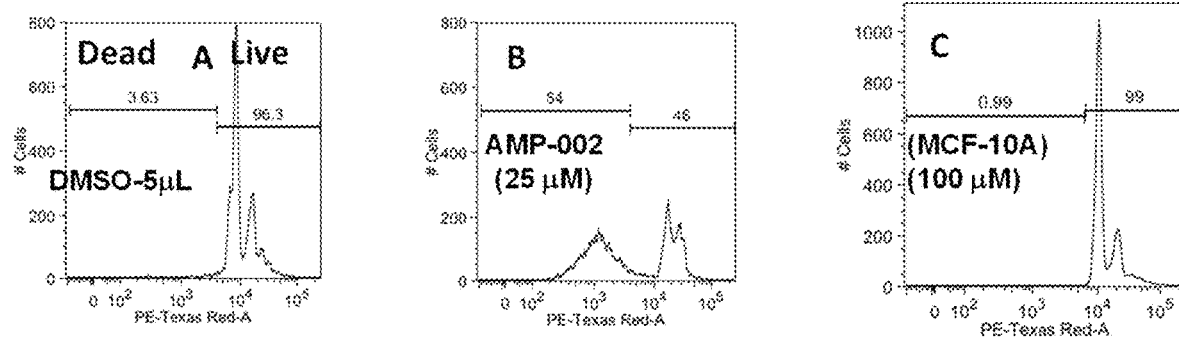
Figure 6: Cancer cell death induction by AMP-002.

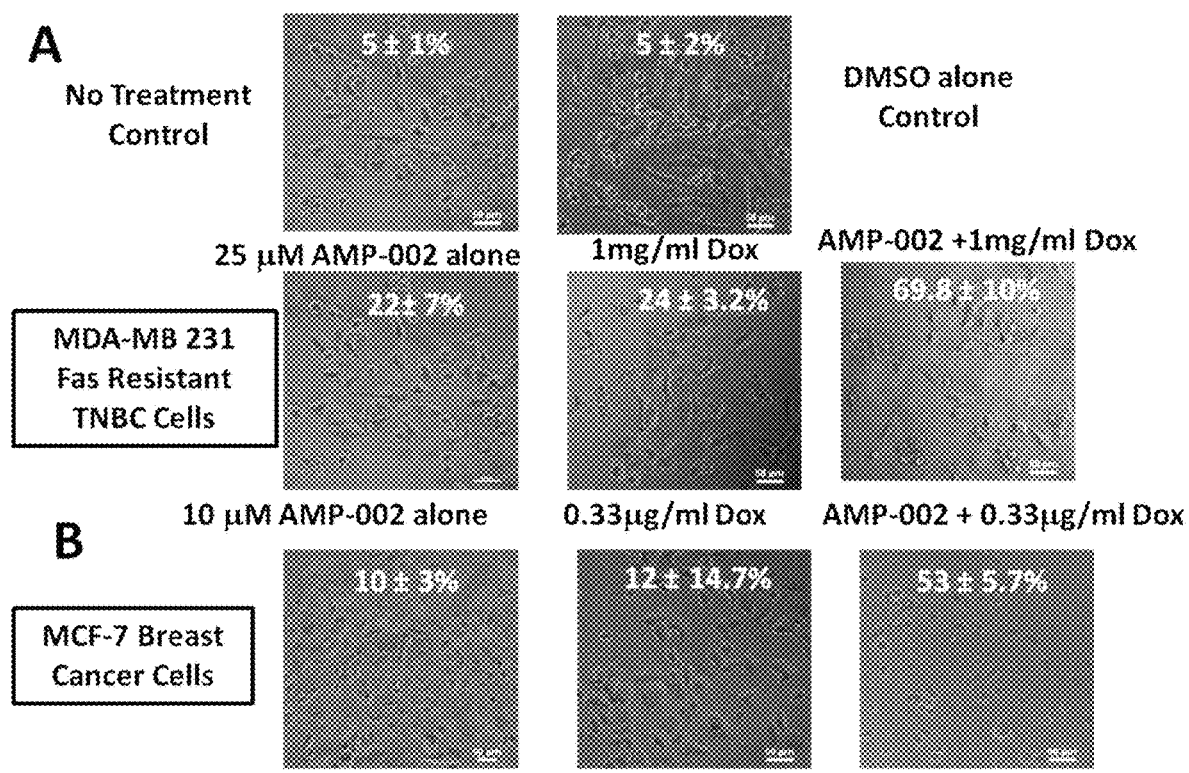
Figure 7. Synergistic cell death effect of AMP-002 and doxorubicin on cancer cells.

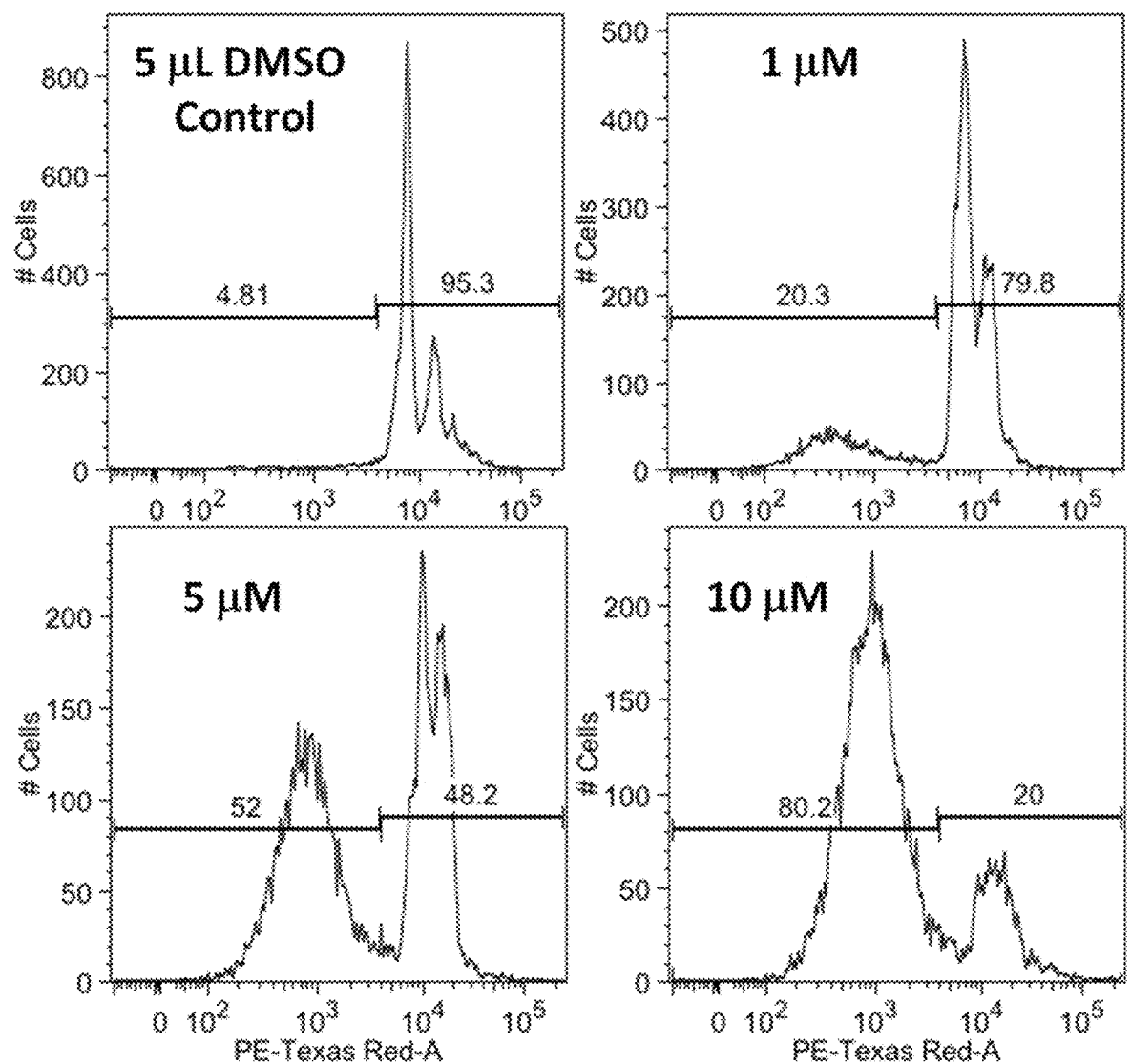
Figure 8. Cancer cell death induction by AMP-003 in triple negative breast cancer cells.

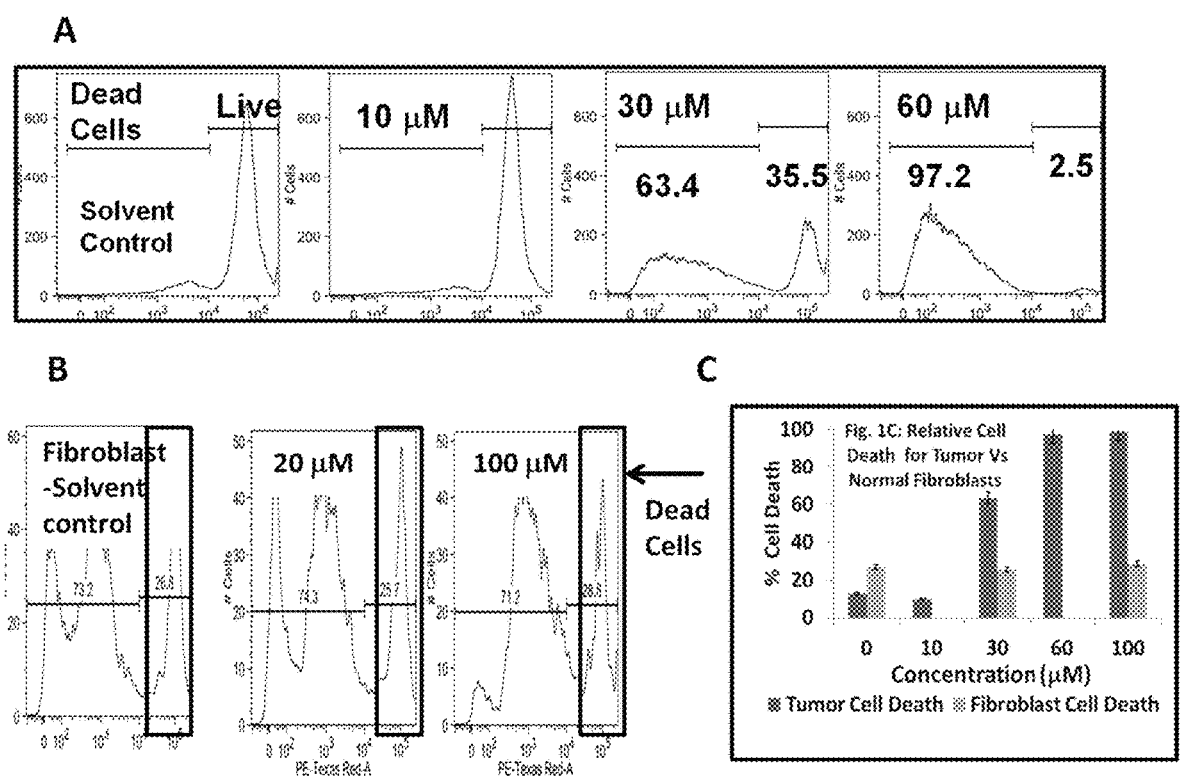
Figure 9. Cancer cell death induction by AMP-004.

1. MDA-MB-231 Triple Negative Breast Cancer Cells
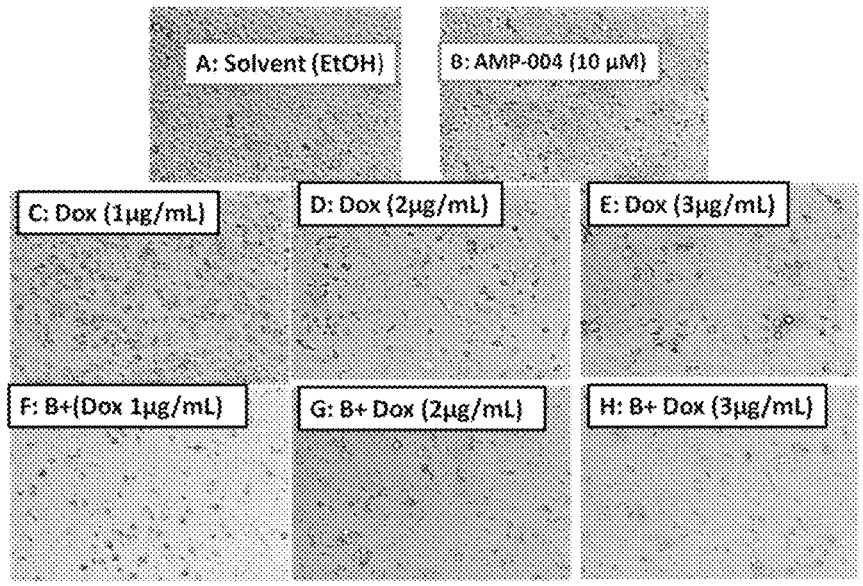
2. PC3 Prostate Cancer Cells
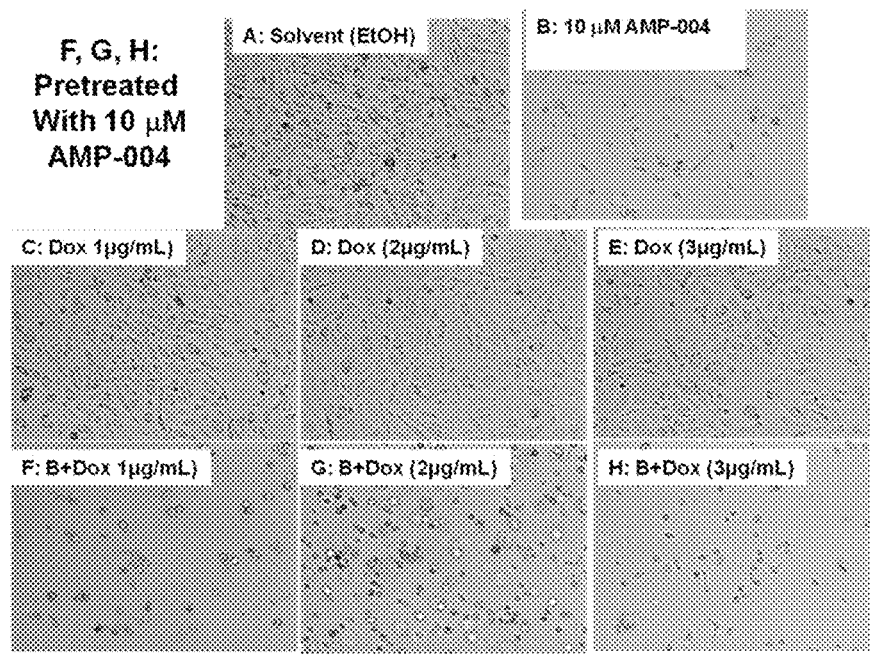
Figure 10. Synergistic cell death effect of AMP-004 and doxorubicin in cancer cells.

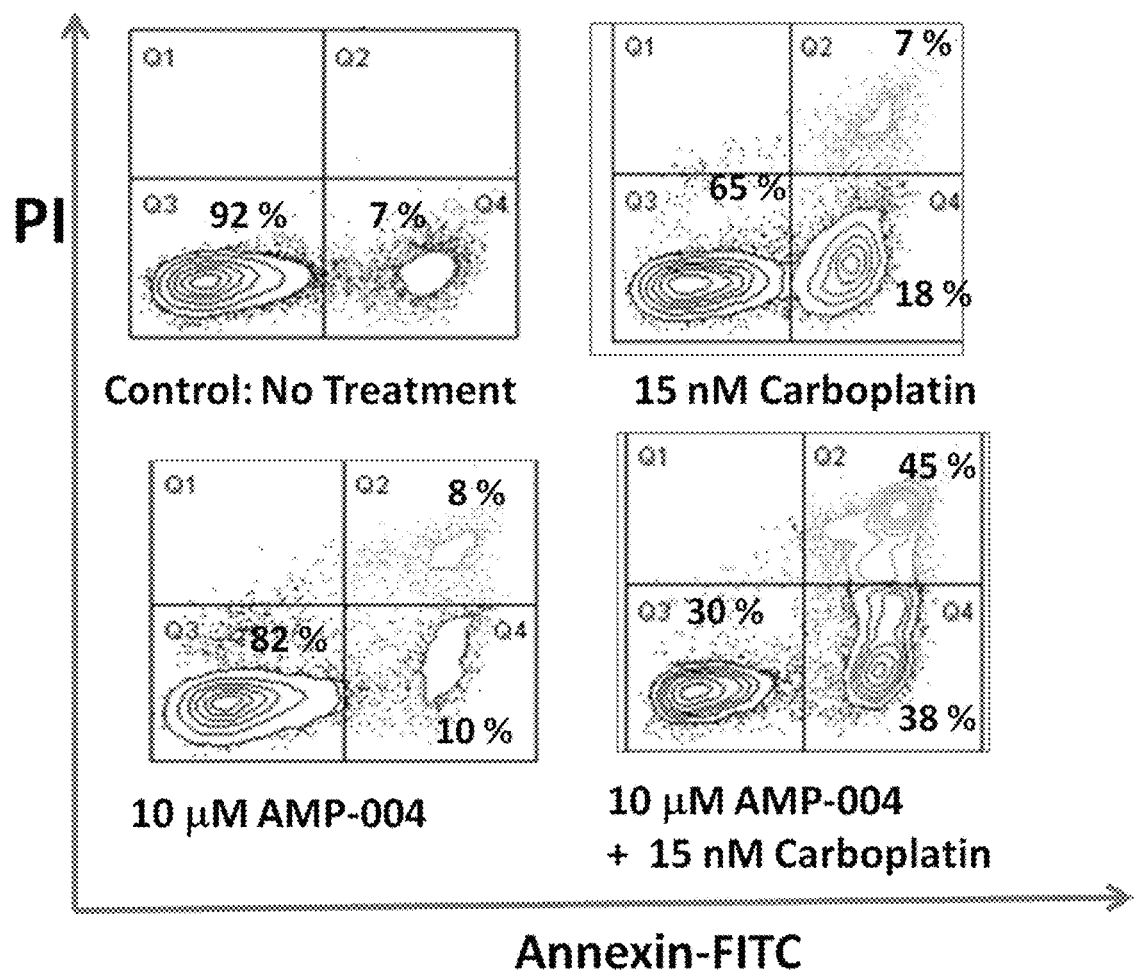
Figure 11. Synergistic effect of AMP-004 with carboplatin in triple negative breast cancer cells.

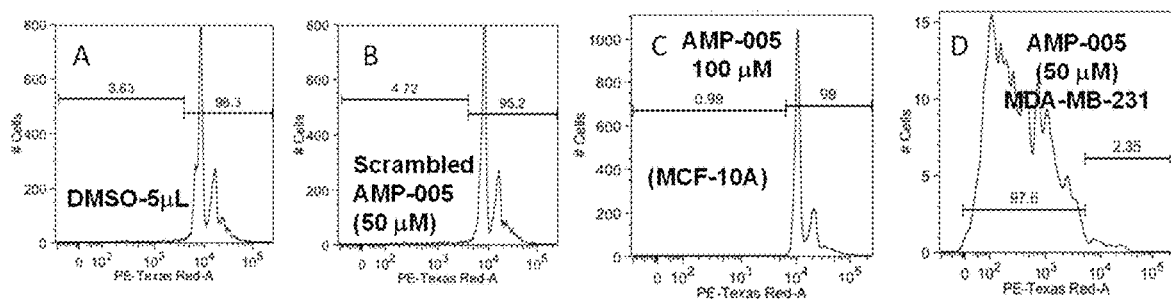
Figure 12. Cancer cell death induction by AMP-005 in triple negative breast cancer cells.

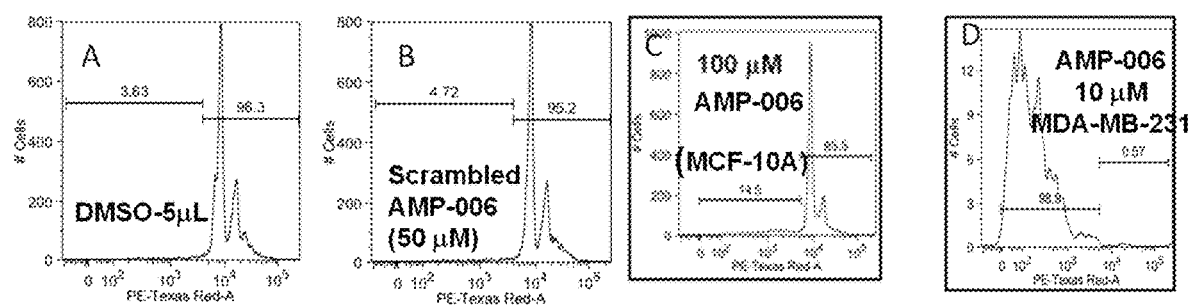
Figure 13. Cancer cell death induction by AMP-006 in triple negative breast cancer cells.

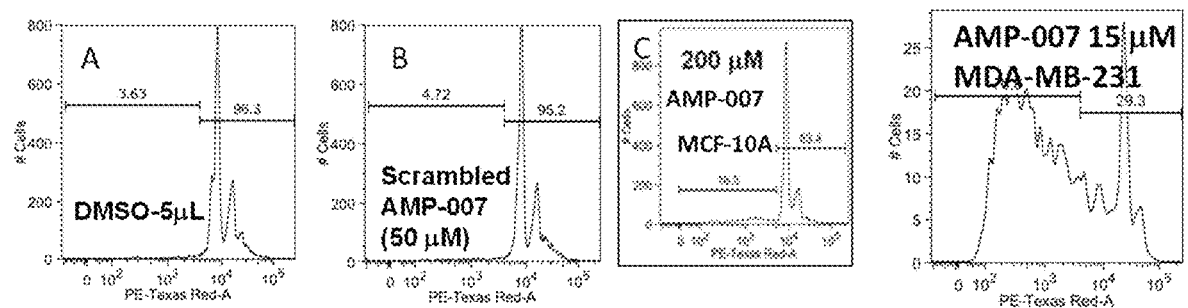
Figure 14. Cancer cell death induction by AMP-007 in triple negative breast cancer cells.

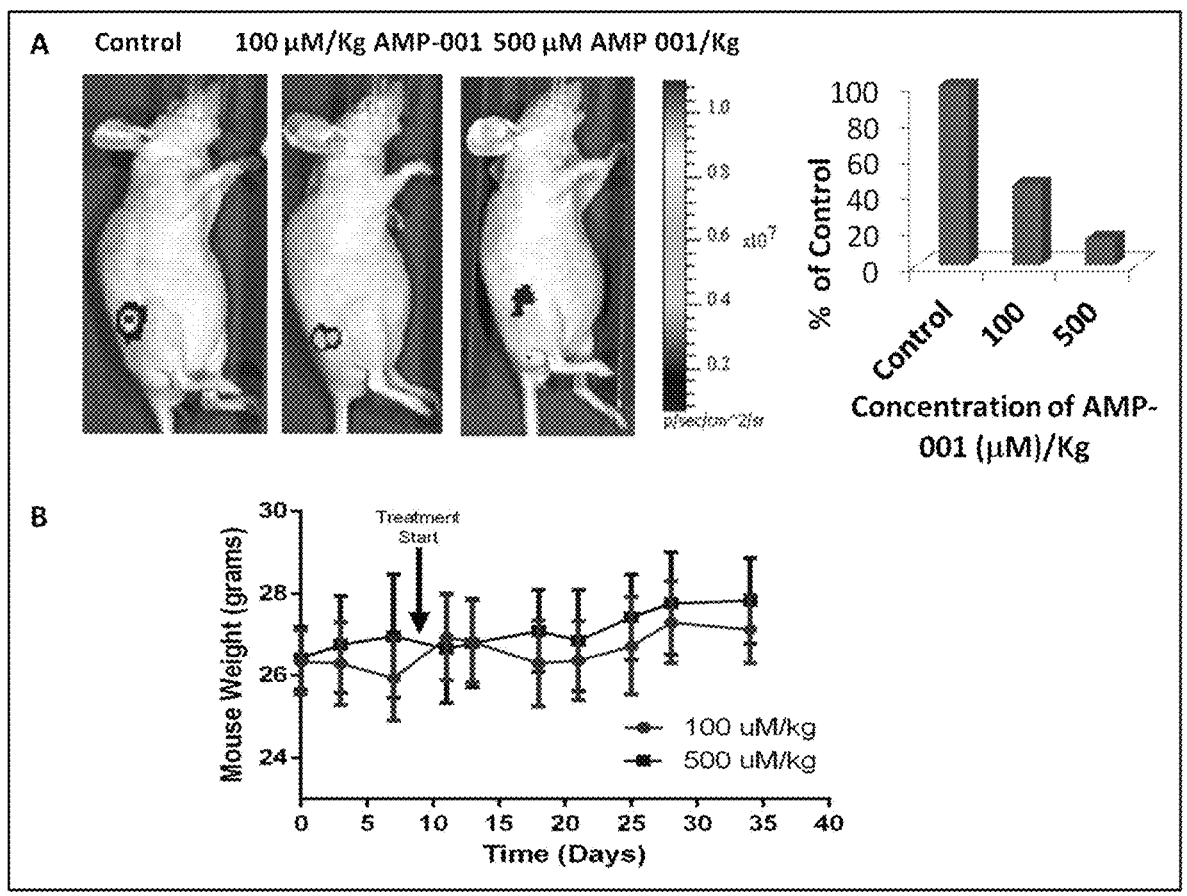
Figure 15. Tissue accumulation and tumor growth inhibitory activity of AMP-001.

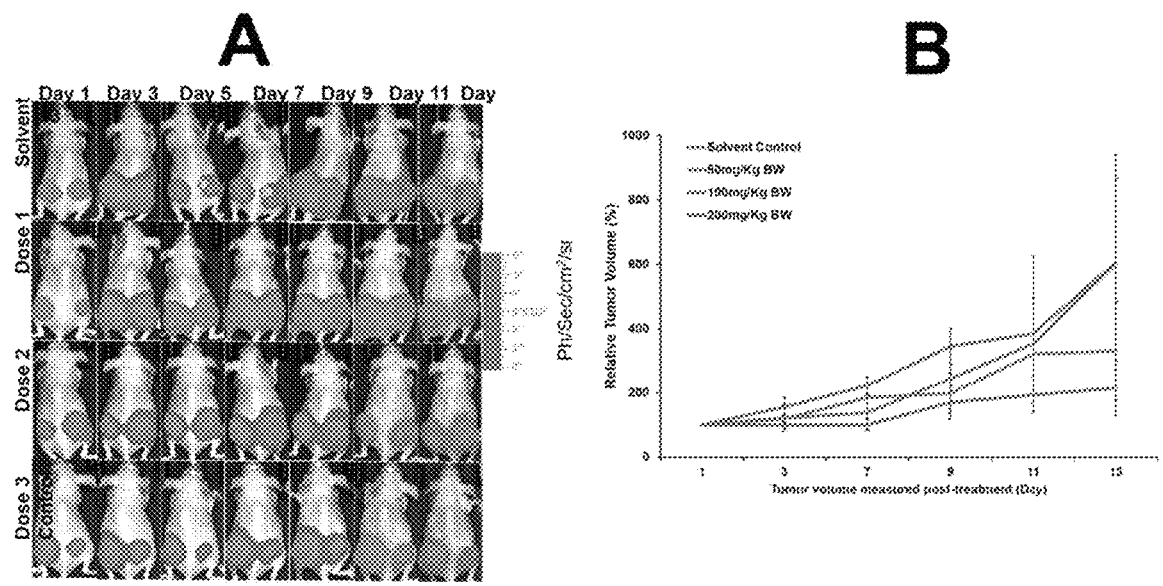
Figure 16. Tumor regression activity of AMP-001 in MDA-MB-231 triple negative breast cancer animal model.

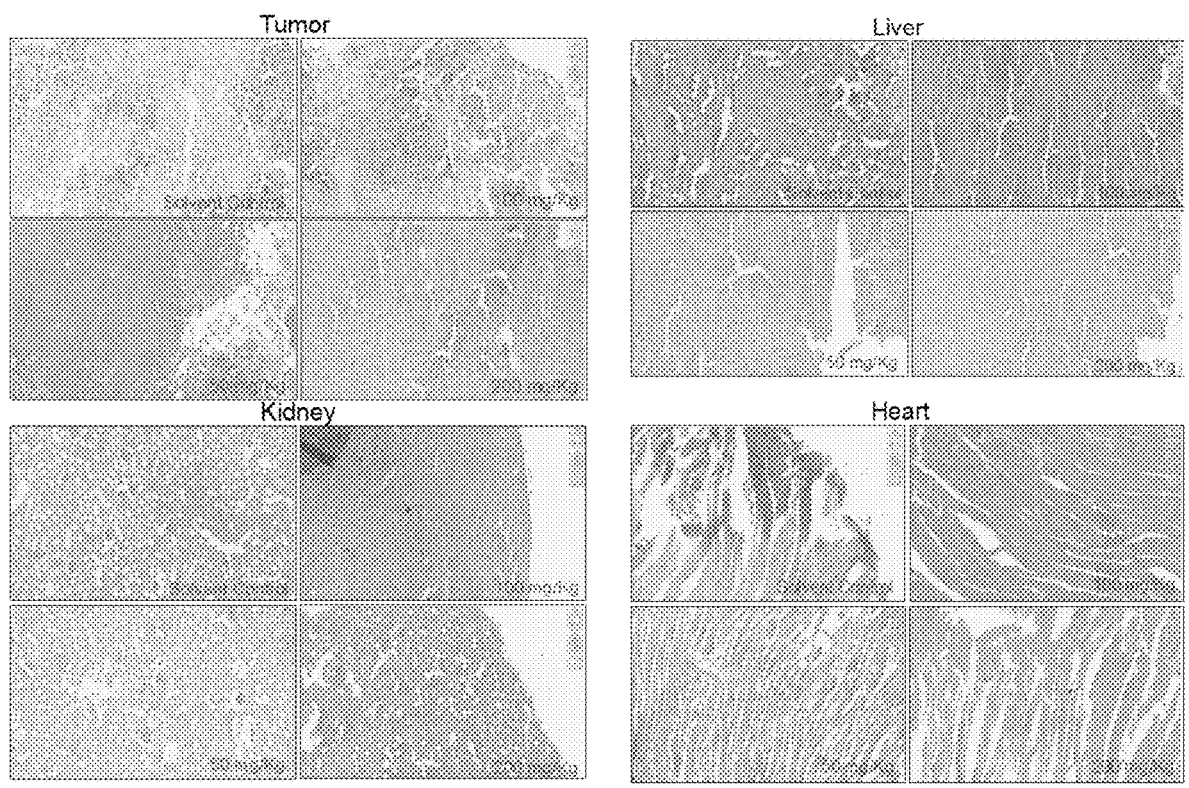
Figure 17. Ex Vivo histological studies on tissues post-treated with AMP-001.

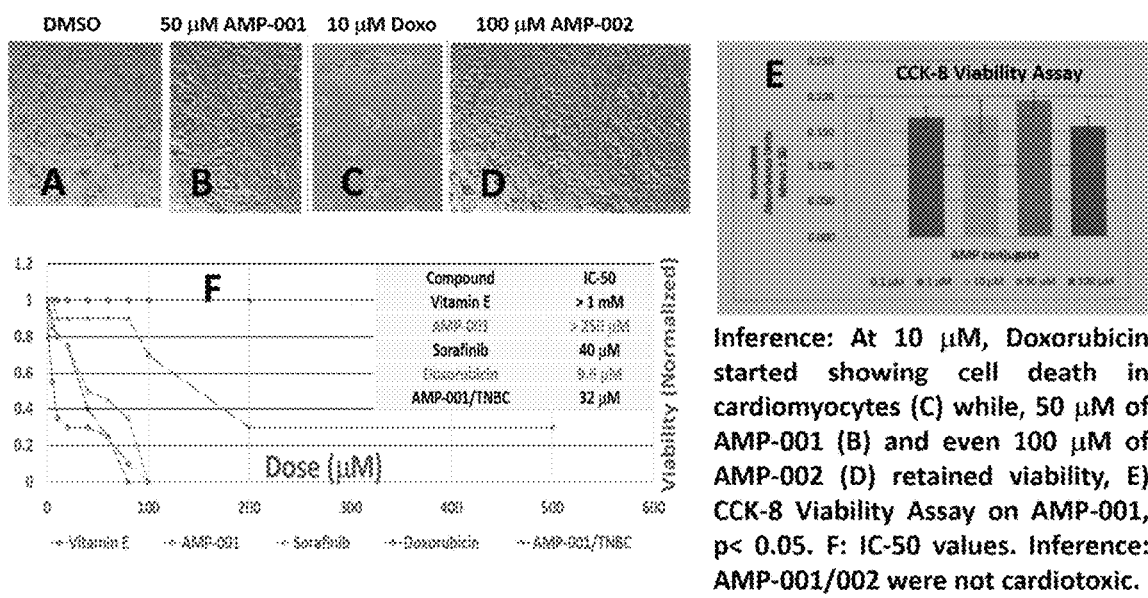
Figure 18. Assessment of cardiotoxicity of AMP-001 and AMP-002 conjugates in adult human heart cell culture.

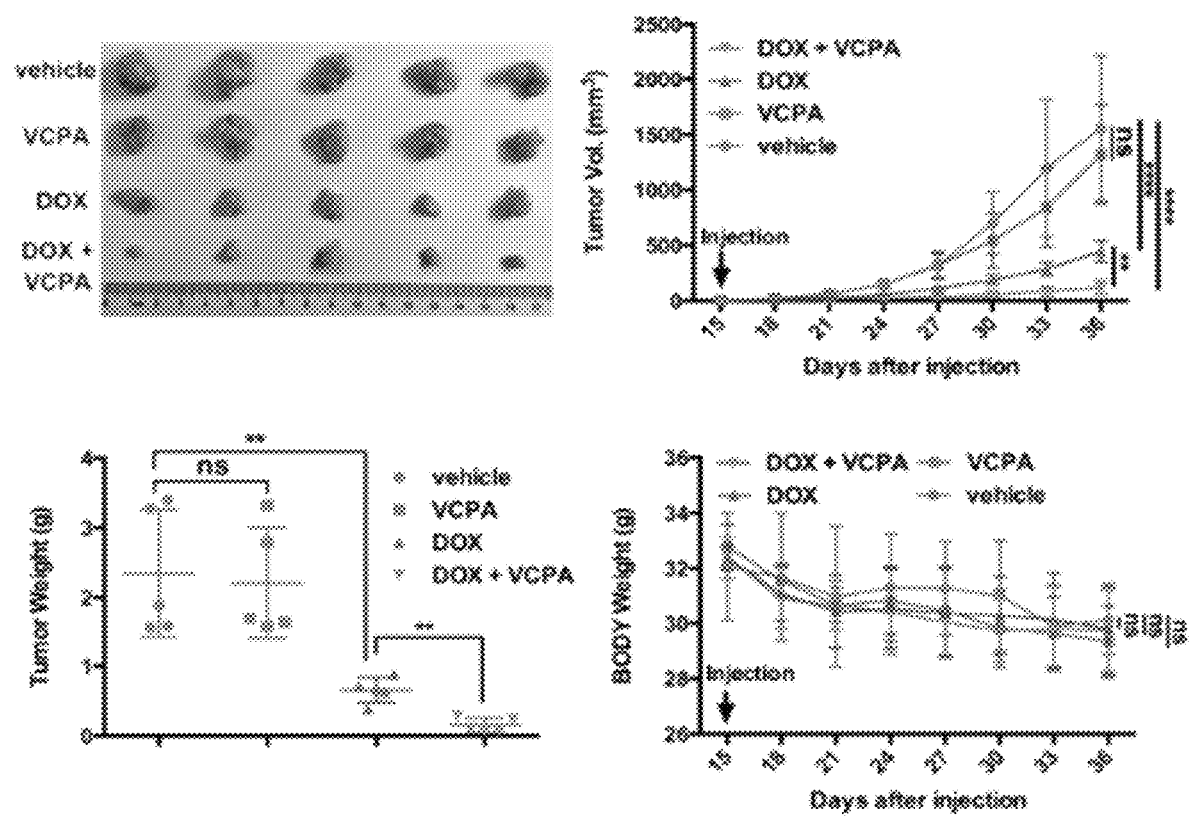
Figure 19: Synergy of AMP-001 (VCPA) and doxorubicin in gastric cancer animal model.

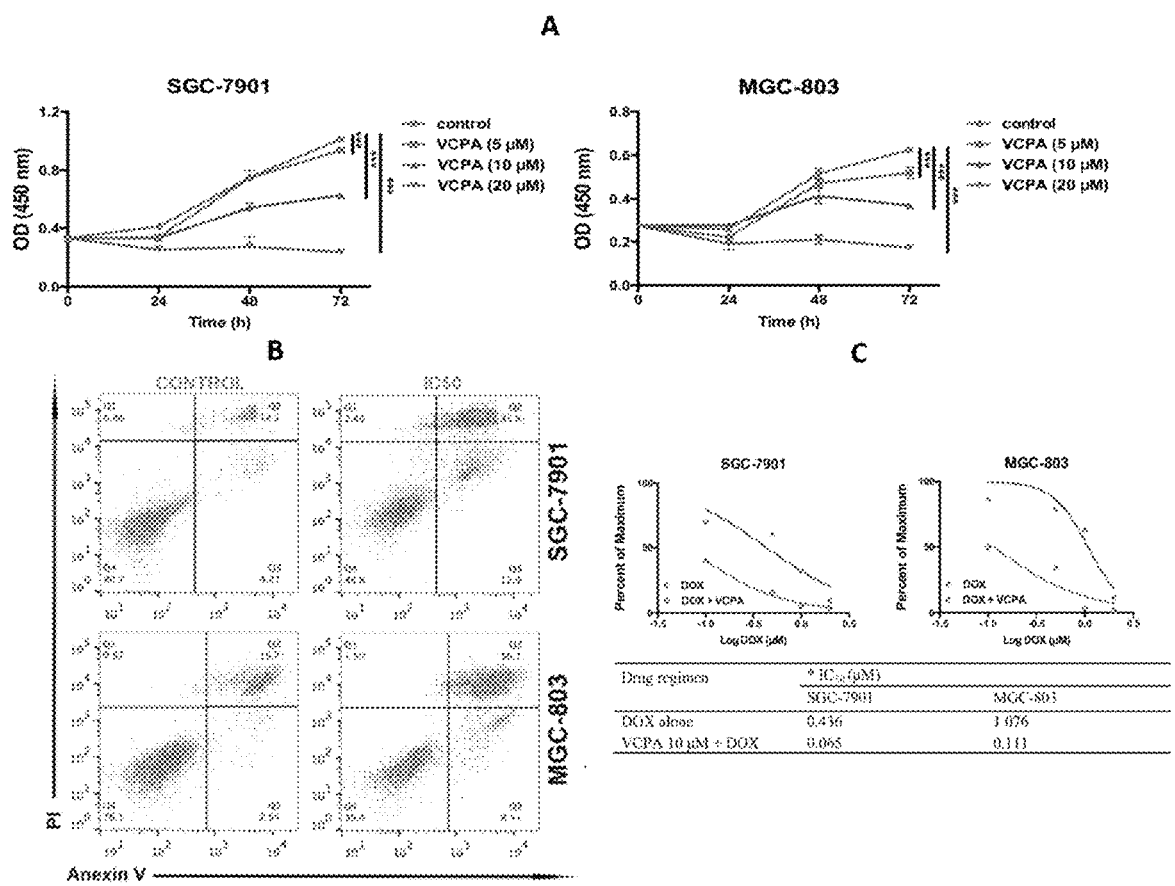
Figure 20. Effect of AMP-001 alone and in combination with DOX on human gastric cancer cells.

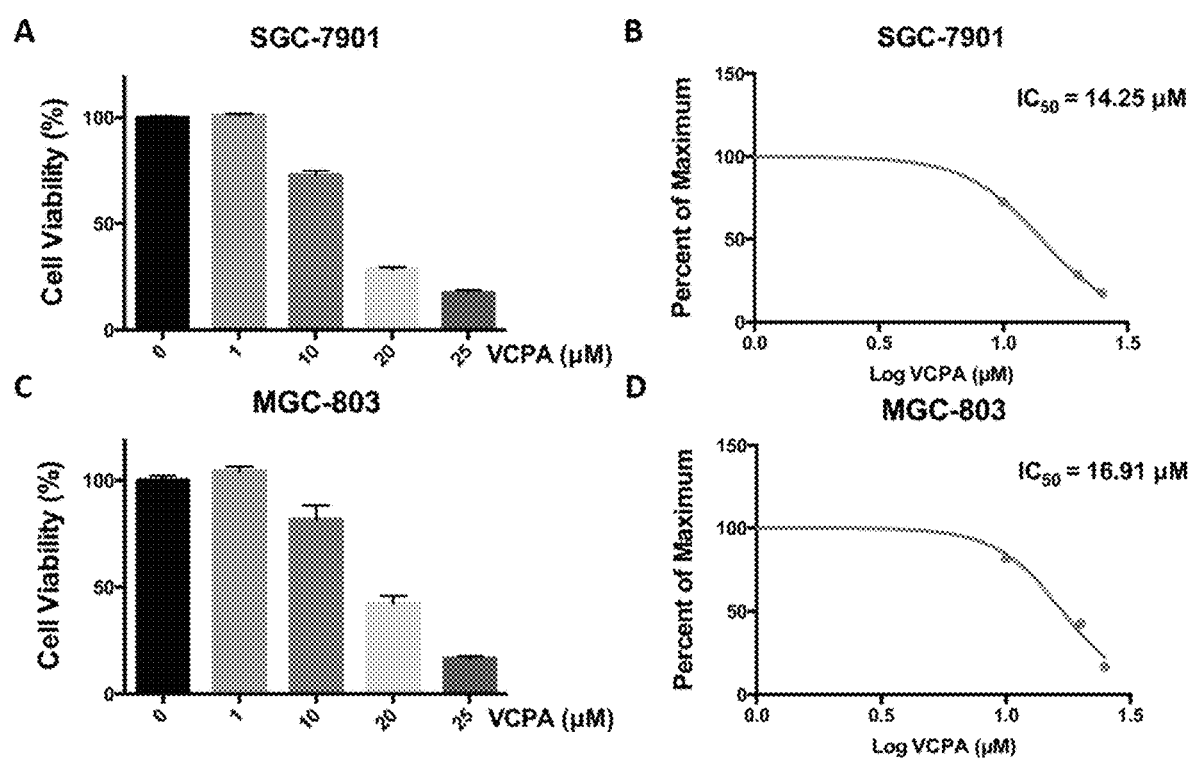
Figure 21. IC$_{50}$ of AMP-001 (VCPA) in gastric cancer cell lines.

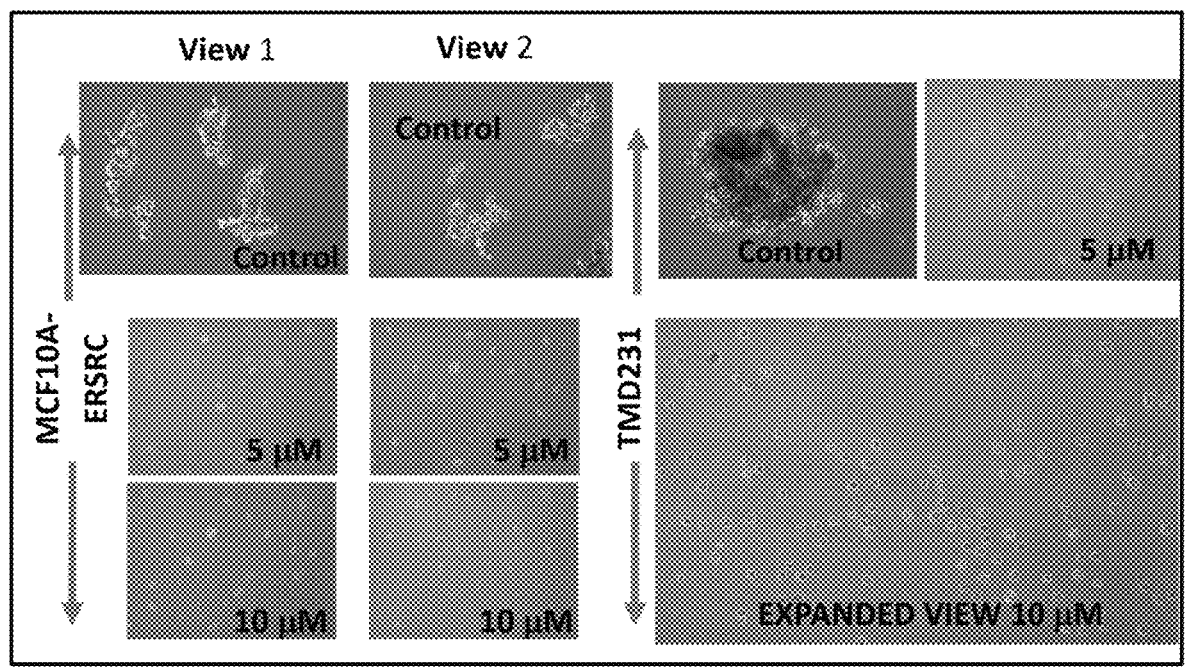
Figure 22. Inhibition of mammosphere formation by AMP-001 in cancer stem cells.

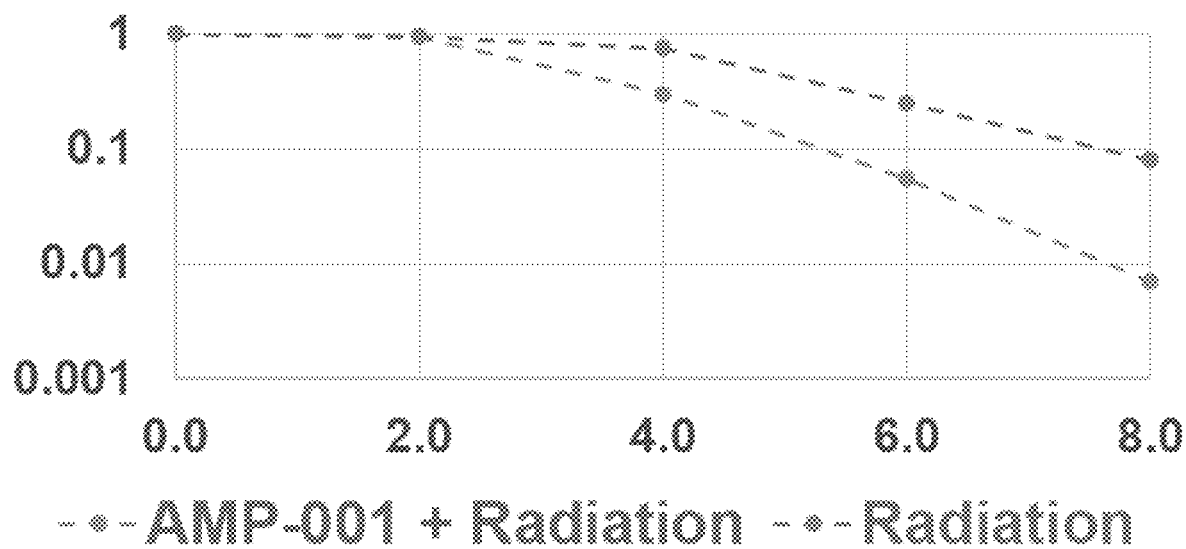
Figure 23: Radiosensitization of triple negative breast cancer cells by AMP-001.

```
SEQUENCE LISTING

<160> NUMBER OF SEQ ID NOS: 9

<210> SEQ ID NO 1
<211> LENGTH: 36
<212> TYPE: PRT
<213> ORGANISM: Artificial Sequence
<220> FEATURE:
<223> OTHER INFORMATION: Human Beta Defensin
<220> FEATURE:
<221> NAME/KEY: DISULFID
<222> LOCATION: (5)..(34)
<220> FEATURE:
<221> NAME/KEY: DISULFID
<222> LOCATION: (12)..(27)
<220> FEATURE:
<221> NAME/KEY: DISULFID
<222> LOCATION: (17)..(35)

<400> SEQUENCE: 1

Asp His Tyr Asn Cys Val Ser Ser Gly Gly Gln Cys Leu Tyr Ser Ala
1               5                   10                  15
```

```
Cys Pro Ile Phe Thr Lys Ile Gln Gly Thr Cys Tyr Arg Gly Lys Ala
            20                  25                  30

Lys Cys Cys Lys
        35
```

<210> SEQ ID NO 2
<211> LENGTH: 10
<212> TYPE: PRT
<213> ORGANISM: Artificial Sequence
<220> FEATURE:
<223> OTHER INFORMATION: MMP-2 Cleavable Linker
<220> FEATURE:
<221> NAME/KEY: MISC_FEATURE
<222> LOCATION: (1)..(1)
<223> OTHER INFORMATION: N-Acetylglutamic acid
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (8)..(8)
<223> OTHER INFORMATION: Homophenylalanine

<400> SEQUENCE: 2

```
Xaa Gly Gly Gly Pro Xaa Gly Xaa Tyr Leu
1               5                   10
```

<210> SEQ ID NO 3
<211> LENGTH: 46
<212> TYPE: PRT
<213> ORGANISM: Artificial Sequence
<220> FEATURE:
<223> OTHER INFORMATION: AMP-004
<220> FEATURE:
<221> NAME/KEY: DISULFID
<222> LOCATION: (1)..(1)
<223> OTHER INFORMATION: N-Acetylglutamic acid
<220> FEATURE:
<221> NAME/KEY: DISULFID
<222> LOCATION: (6)..(6)
<223> OTHER INFORMATION: Citrulline
<220> FEATURE:
<221> NAME/KEY: DISULFID
<222> LOCATION: (8)..(8)
<223> OTHER INFORMATION: Homophenylalanine
<220> FEATURE:
<221> NAME/KEY: DISULFID
<222> LOCATION: (15)..(44)
<220> FEATURE:
<221> NAME/KEY: DISULFID
<222> LOCATION: (22)..(37)
<220> FEATURE:
<221> NAME/KEY: DISULFID
<222> LOCATION: (27)..(45)

<400> SEQUENCE: 3

```
Xaa Gly Gly Gly Pro Xaa Gly Xaa Tyr Leu Asp His Tyr Asn Cys Val
1               5                   10                  15

Ser Ser Gly Gly Gln Cys Leu Tyr Ser Ala Cys Pro Ile Phe Thr Lys
            20                  25                  30

Ile Gln Gly Thr Cys Tyr Arg Gly Lys Ala Lys Cys Cys Lys
        35                  40                  45
```

<210> SEQ ID NO 4
<211> LENGTH: 9
<212> TYPE: PRT
<213> ORGANISM: Artificial Sequence
<220> FEATURE:
<223> OTHER INFORMATION: Octreotate

```
<220> FEATURE:
<221> NAME/KEY: MISC_FEATURE
<222> LOCATION: (1)..(1)
<223> OTHER INFORMATION: d-Phenylalanine
<220> FEATURE:
<221> NAME/KEY: DISULFID
<222> LOCATION: (2)..(6)
<220> FEATURE:
<221> NAME/KEY: MISC_FEATURE
<222> LOCATION: (4)..(4)
<223> OTHER INFORMATION: d-Tryptophan
<220> FEATURE:
<221> NAME/KEY: MISC_FEATURE
<222> LOCATION: (9)..(9)
<223> OTHER INFORMATION: Citrulline

<400> SEQUENCE: 4

Xaa Cys Tyr Xaa Lys Cys Thr Val Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: AMP-008
<220> FEATURE:
<221> NAME/KEY: DISULFID
<222> LOCATION: (1)..(13)

<400> SEQUENCE: 5

Cys Tyr Val Gln Arg Lys Arg Gln Arg Leu Met Pro Cys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: AMP-013
<220> FEATURE:
<221> NAME/KEY: DISULFID
<222> LOCATION: (1)..(8)

<400> SEQUENCE: 6

Cys Arg Gly Phe Arg Arg Arg Cys Arg
1               5

<210> SEQ ID NO 7
<211> LENGTH: 12
<212> TYPE: PRT
<213> ORGANISM: Artificial Sequence
<220> FEATURE:
<223> OTHER INFORMATION: AMP-014
<220> FEATURE:
<221> NAME/KEY: DISULFID
<222> LOCATION: (1)..(9)
<220> FEATURE:
<221> NAME/KEY: MISC_FEATURE
<222> LOCATION: (11)..(11)
<223> OTHER INFORMATION: Citrulline

<400> SEQUENCE: 7

Cys Ile Phe Leu Leu Trp Gln Arg Cys Val Xaa Arg
1               5                   10

<210> SEQ ID NO 8
<211> LENGTH: 10
<212> TYPE: PRT
<213> ORGANISM: Artificial Sequence
<220> FEATURE:
```

```
<223> OTHER INFORMATION: AMP-005 To AMP-007
<220> FEATURE:
<221> NAME/KEY: DISULFID
<222> LOCATION: (2)..(6)
<220> FEATURE:
<221> NAME/KEY: MISC_FEATURE
<222> LOCATION: (4)..(4)
<223> OTHER INFORMATION: d-Phenylalanine
<220> FEATURE:
<221> NAME/KEY: MISC_FEATURE
<222> LOCATION: (7)..(7)
<223> OTHER INFORMATION: d-Tryptophan
<220> FEATURE:
<221> NAME/KEY: MISC_FEATURE
<222> LOCATION: (10)..(10)
<223> OTHER INFORMATION: Citrulline

<400> SEQUENCE: 8

Thr Cys Lys Xaa Tyr Cys Xaa Asp Val Xaa
1               5                   10

<210> SEQ ID NO 9
<211> LENGTH: 4
<212> TYPE: PRT
<213> ORGANISM: Artificial Sequence
<220> FEATURE:
<223> OTHER INFORMATION: AMP-012
<220> FEATURE:
<221> NAME/KEY: MISC_FEATURE
<222> LOCATION: (1)..(1)
<223> OTHER INFORMATION: Citrulline
<220> FEATURE:
<221> NAME/KEY: MISC_FEATURE
<222> LOCATION: (4)..(4)
<223> OTHER INFORMATION: Citrulline

<400> SEQUENCE: 9

Xaa Val Val Xaa
1
```

COMPOSITIONS AND METHODS FOR SENSITIZING LOW RESPONSIVE TUMORS TO CANCER THERAPY

CROSS-REFERENCE TO RELATED APPLICATIONS

This is a request for continued examination application of the parent non-provisional application Ser. No. 15/749,225 filed on Jan. 31, 2018. This application claims benefit of priority based on provisional application No. 62/287,221 filed on Jan. 26, 2016.

STATEMENT REGARDING FEDERALLY SPONSORED RESEARCH OR DEVELOPMENT

The research work related to the subject matter of the present application was carried out under the Small Business Innovation Research grant No. R43CA183353 from the National Cancer Institute of National Institute of Health.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

Field of the Invention

This invention relates to the compositions and methods to enhance the susceptibility of cancer cells toward anti-cancer agents, chemotherapeutic, radiotherapeutic, and immunotherapeutic. Particularly, this invention relates to novel compositions capable of selectively sensitizing poorly responding tumor cells prior to the administration of therapeutic regimen in order to enhance the potency of said therapeutic agents.

Description of the Related Art

Various prior art references in the specification are indicated by italicized Arabic numerals in brackets. Full citation corresponding to each reference number is listed at the end of the specification, and is herein incorporated by reference in its entirety in order to describe fully and clearly the state of the art to which this invention pertains.

Unless otherwise specified, all technical terms and phrases used herein conform to standard organic, medicinal, and bioconjugate chemistry nomenclature established by International Union of Pure and Applied Chemistry (IUPAC), American Chemical Society (ACS), and other international professional societies.

Cancer cells also have a remarkable ability to survive, proliferate, and metastasize by evading the cell death pathways. Dysregulation of apoptosis pathway or the loss of apoptotic propensity of cells is the early step of oncogenesis and plays a significant role in nearly all cancers [1]. The extent of dysregulation, as measured through spontaneous apoptosis level of tumor (referred to as 'apoptotic index, or 'AI', FIG. 1) determines the extent to which the tumors respond to therapy, irrespective of the nature of therapy [2]. Furthermore, it is well established that there is a direct correlation between the apoptotic index of a tumor and its response to therapeutic intervention as shown in FIG. 1. For example, spontaneous apoptosis of hepetocelluar (HCa-1) and ovarian (OCa-1) carcinoma is 0.6% and 5% respectively and consequently, the response of HCa-1 to treatment was minimal or in these tumors despite the fact that the radiation dose to HCa-1 was increased 10 fold. Also, the overall 5-year survival rates post treatment for the patients belonging to the group with high AI follows a similar pattern in that those cancer patients exhibiting low apoptotic index has lower survival rate that those having high apoptotic index [3]. Thus, there is a need to develop effective technologies to treat poorly responsive cancers.

Tumor sensitivity to chemotherapy in vivo is shown to be dependent on spontaneous baseline tumor apoptosis index. In general, the higher the baseline apoptosis index, the better are the responses from chemotherapy and vice versa. Aggressive or incurable cancers show low tumor apoptosis index, high loss of apoptosis capability, and low sensitivity to therapeutic intervention [4]. Therefore, reactivating cell death pathways back to basal level selectively in tumor cells will enhance the susceptibility of tumor cells thereby evoking a better response from therapeutic intervention. However, ubiquitous activation of apoptosis has been shown to have serious side effects, such as the development of neurodegenerative diseases [5]. Hence, it is necessary to activate the apoptosis pathway selectively in tumors before application of any therapeutic regimen so that the susceptibility of low-responding tumors to therapy can be substantially increased without affecting the normal cells.

BRIEF SUMMARY OF THE INVENTION

Accordingly, the present invention discloses compositions and methods for selectively delivering apoptosis inducing agents (referred to as 'apoptogens') to the tumor prior to conventional therapeutic treatment protocol. We refer to this technology as 'a priori activation of apoptosis pathways of tumors (AAAPT).' Specifically, the present invention relates to an ensemble (or 'bioconjugate') comprising of an apoptogen (A) and a tumor targeting group (or vector) (T), wherein the apoptogen is either connected directly to the targeting group or optionally attached through an intervening linker (L), as described schematically below. The

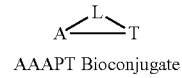

AAAPT Bioconjugate apoptogen (A) may be a small or large molecule that activates apoptosis pathway and causes cell death. The targeting vector (T) may be a small or large molecule that delivers the apoptogen selectively to the tumors. The linker (L) may comprise simple alkylene chain or may contain functional groups that are capable of being cleaved by enzymatic process. In some embodiment the apoptogen may also simultaneously serve as the targeting vector. For example, human beta defensin is known to enter the cell via cell surface receptor mediated endocytosis [6] and, as we will demonstrate later, deactivates thioredoxin enzyme that is involved in apoptosis [7]. In some other embodiment, the enzyme-cleavable linker may also serve as a targeting group. For example, cathepsin B and MMP-2 are overexpressed in many cancers. Thus, the AAAPT bioconjugate bearing a linker capable of being cleaved by these enzymes is expected to induce much higher death of tumor cells compared to the normal cells. As will be demonstrated later, the AAAPT conjugates of the present invention do induce large synergistic and selective cancer cell death response in combination with therapeutic agents.

BRIEF DESCRIPTION OF THE SEVERAL VIEWS OF THE DRAWING(S)

FIG. 1. Apoptosis index. Apoptosis index correlated to response from anticancer agents.

FIG. 2A. Structures of some embodiments of AAAPT compounds (AMP-001 to AMP-004). Sheet 2—AMP-004, SEQ ID. NO: 003.

FIG. 2B. Structures of some embodiments of AAAPT compounds (AMP-005 to AMP-007). Sheet 3—AMP-005, AMP-006, and AMP-007, SEQ ID. NO: 004.

FIG. 2C. Structures of some embodiments of AAAPT compounds (AMP-008 to AMP-012). Sheet 4—AMP-008, SEQ ID. NO: 005.

FIG. 2D. Structures of some embodiments of AAAPT compounds (AMP-013 to AMP-016). Sheet 5—AMP-013, SEQ ID. NO: 006. Sheet 5—AMP-014, SEQ ID. NO: 007.

FIG. 3A. General synthetic scheme for the preparation of AAAPT AMP-001.

FIG. 3B. General synthetic scheme for the preparation of AAAPT AMP-002 and AMP-003.

FIG. 3C: General synthetic scheme for the preparation of AAAPT bioconjugates, AMP-004 to AMP-007. Sheet 8—AMP-004: MMP-2 cleavable peptide Sequence ID No. 002; p3-defensin peptide Sequence ID No. 001. Sheet 8—AMP-005: Octreotate peptide Sequence ID No. 004, Apoptosis Initiator=AMP-001. Sheet 8—AMP-006: Octreotate peptide Sequence ID No. 004, Apoptosis Initiator=AMP-002. Sheet 8—AMP-007: Octreotate peptide Sequence ID No. 004, Apoptosis Initiator=AMP-003. All apoptosis initiators were conjugated to the C-terminal of citrulline using HBTU/HOBt coupling agent. Peptides were synthesized using peptide synthesizer.

FIG. 4. Cell death induction by AMP-001. (a) Apoptosis induction by AMP-001 in MDA-MB-231 triple negative breast cancer cells, (b) Apoptosis induction by AMP-001 in normal fibroblasts cells.

FIG. 5. Synergistic cell death effect of AMP-001 and doxorubicin on cancer cells. (a) MDA-MB-231 triple negative breast cancer cells, (b) Tumor cells derived from patient cells.

FIG. 6: Cancer cell death induction by AMP-002. (a) Apoptosis induction by AMP-002 in DMSO control, (b) Apoptosis induction by AMP-001 in triple negative breast cancer MDA-MB-231 cells, and (c) Normal epithelial breast cancer cells (MCF-10A).

FIG. 7. Synergistic cell death effect of AMP-002 and doxorubicin in (a) MDA-MB-231 triple negative breast cancer (TNBC) cells, and (b) MCF-7 (TNBC) cancer cells.

FIG. 8. Cancer cell death induction by AMP-003 in MDA-MB-231 triple negative breast cancer cells.

FIG. 9. Cancer cell death induction by AMP-004. (a) MDA-MB-231 triple negative breast cancer cells, (b) normal fibroblasts, and (c) normal fibroblasts compared to cancer cells.

FIG. 10. Synergistic cell death effect of AMP-004 and doxorubicin in cancer cells. (a) MDA-MB-231 triple negative breast cancer cells, and (b) PC3 prostate cancer cells.

FIG. 11. Synergistic effect of AMP-004 with carboplatin in MDA-MB-231 triple negative breast cancer cells.

FIG. 12. Cancer cell death induction by AMP-005 in triple negative breast cancer cells. (A) Vehicle control, (B) Scrambled AMP-005 in MDA-MB-231 cells, (C) AMP-005 in normal epithelial breast cells MCF-10A, and (D) AMP-005 in MDA-MB-231 cells.

FIG. 13. Cancer cell death induction by AMP-006 in MDA-MB-231 triple negative breast cancer cells. (A) Vehicle control, (B) Scrambled AMP-006 in MDA-MB-231 cells, (C) AMP-006 in normal epithelial breast cells MCF-10 A, and (D) AMP-006 in MDA-MB-231 cells.

FIG. 14. Cancer cell death induction by AMP-007 in MDA-MB-231 triple negative breast cancer cells. (A) Vehicle control, (B) Scrambled AMP-007 in MDA-MB-231 cells, (C) AMP-007 in normal epithelial breast cells MCF-10 A, and (D) AMP-007 in MDA-MB-231 cells.

FIG. 15. Tissue accumulation and tumor growth inhibitory activity of AMP-001. (a) In vivo MDA-MB-231-luc xenograft model. (b) Mice weight loss monitoring for 100 µM/kg and 500 µM/Kg dose for 41 days.

FIG. 16. Tumor regression activity of AMP-001 in MDA-MB-231 triple negative breast cancer animal model.

FIG. 17. Ex vivo histological studies on tissues of mice post-treated with AMP-001.

FIG. 18. Assessment of cardiotoxicity of AMP-001 and AMP-002 conjugate in adult human heart cell culture. Comparison of $IC_{50}$ values for AMP-001 compared to doxorubicin and standard Sorafinib. The higher $IC_{50}$ value for AMP-001 in cardiomyocytes (>250 PM) compared to doxorubicin (9.6 µM) clearly demonstrates better safety profile for AMP-001. Photomicrographs of the morphology of cardiomyocytes showed that either 50 µM AMP-001 or 100 µM AMP-002 retained viability while, 10 µM doxorubicin resulted in cell death.

FIG. 19. Synergy of AMP-001 (VCPA) and doxorubicin in gastric cancer animal model.

FIG. 20. Effect of AMP-001 alone and in combination with DOX on human gastric cancer cells. (A) AMP-001 (VCPA) suppresses the growth of human gastric cancer cells (SGC-7901 and MGC-803) (B) AMP-001 (VCPA) induces apoptosis in human gastric cancer cells SGC-7901 and MGC-803, (C) $IC_{50}$ drift of DOX only or AMP-001 (VCPA)/DOX combination treatment, in gastric cancer cells. Results: (A) Dose dependent AMP-001 reduced the growth of gastric cancer cells back to the base level, (B) induced cell death 48% in SGC-7901 while, it induced 58% in MGC-803 gastric cancer cells (C) $IC_{50}$ of the combination of doxorubicin and AMP-001 is reduced from 0.436 for doxorubicin to 0.065 (almost 10 times less) in SGC-7901 cells and from 1.076 to 0.111 in MGC-803.

FIG. 21. $IC_{50}$ of AMP-001 (VCPA) in gastric cell lines.

FIG. 22. Inhibition of mammosphere formation by AMP-001 in cancer stem cells. (a) MCF-10A breast cells overexpressed with Src oncogene, and (b) TMD-231 cells.

FIG. 23. Radiosensitization of triple negative breast cancer cells MDA-MB-231 cells.

DETAILED DESCRIPTION OF THE INVENTION

The present invention relates to the AAAPT bioconjugate of general Formula 1, wherein $$A-L-T \qquad \text{Formula 1}$$

A may be a small molecule such as, but is not limited to α-tocopherol succinate (1), benzamide riboside (2), bortezomib (3), cycloheximide (4), or hispolone (5) [8-11]; or a macromolecule such as, but not limited to TRAIL [12], or AIF1 Flavoprotein [13]). L is an alkylene or polyoxaalkyene chain selected from the group comprising —OC(CH$_2$)$_a$CO—, —HN(CH$_2$)$_b$CO—, —OC(CH$_2$)$_c$NH—, —(CH$_2$)$_d$NH—, —NH(CH$_2$)$_e$—, —O(CH$_2$)$_f$(CH$_2$CH$_2$O)$_g$(CH$_2$)$_h$O—, —OC(CH$_2$)$_i$(CH$_2$CH$_2$O)$_j$(CH$_2$)$_k$CO—, and —HN(CH$_2$)$_i$(CH$_2$CH$_2$O)$_j$(CH$_2$)$_k$NH—. L may optionally contain an acid cleavable or an enzymatically cleavable polypeptide sequences. T is selected from the group comprising somatostatin receptor binding agents, folate receptor binding agents, cathepsin B binding agents, matrix metalloprotein-2 (MMP-2) binding agents, GRP receptors, estrogen receptors, epidermal growth factor receptors (EGFR), and benzodiazepine.

The present invention also relates to the AAAPT bioconjugate of general Formula 2, $$A\text{—}T \qquad \text{Formula 2}$$

wherein A may be a small molecule such as, but is not limited to α-tocopherol succinate (1), benzamide riboside (2), bortezomib (3), cycloheximide (4), or hispolone (5) [8-11]; or a macromolecule such as, but not limited to TRAIL [12], or AIF1 Flavoprotein [13]). L may optionally contain acid enzymatically cleavable polypeptide sequences. T is selected from the group comprising somatostatin receptor binding agents, folate receptor binding agents, cathepsin B binding agents, matrix metalloprotein-2 (MMP-2) binding agents, GRP receptors, estrogen receptors, epidermal growth factor receptors (EGFR), and benzodiazepine.

One embodiment of the AAAPT bioconjugate of the present invention is represented by Formula 1, wherein A is α-tocopherol; T is cathepsin binding dipeptide, Val-Cit (valine-citrulline); and L is —O(CH$_2$)$_f$(CH$_2$CH$_2$O)$_g$(CH$_2$)$_h$O—.

Another embodiment is represented by Formula 1, wherein A is α-tocopherol; T is cathepsin binding dipeptide, Val-Cit (valine-citrulline); and L is —(CH$_2$)$_d$NH—.

Another embodiment is represented by Formula 1, wherein A is α-tocopherol; T is cathepsin binding dipeptide, Val-Cit (valine-citrulline); and L is —HN(CH$_2$)$_b$CO—.

Another embodiment is represented by Formula 1, wherein A is α-tocopherol; T is cathepsin binding dipeptide, Val-Cit (valine-citrulline); and L is —OC(CH$_2$)$_a$CO—.

Another embodiment is represented by Formula 1, wherein A is α-tocopherol; T is octreotate; and L is val-cit-HN(CH$_2$)$_e$—.

Another embodiment is represented by Formula 1, wherein A and T are simultaneously human defensin-1 protein having SEQ ID NO: 001, wherein disulfide bonds are formed between each pair of cysteines 5 and 34, 12 and 27, and 17 and 35; and L is MMP-2 enzyme cleavable peptide having SEQ ID NO: 002, wherein Xaa at position 1 is N-acetylglutamic acid and at positions 6 and 8 are citrulline (Cit) and homophenylalanine (Hof) respectively.

```
                                        SEQ ID NO: 001
Asp His Tyr Asn Cys Val Ser Ser Gly Gly Gln Cys Leu
1               5               10
Tyr Ser Ala Cys Pro Ile Phe Thr Lys Ile Gln Gly Thr
     15              20  21              25
Cys Tyr Arg Gly Lys Ala Lys Cys Cys Lys.
             30              35

SEQ ID NO: 002
Xaa Glu Glu Glu Pro Xaa Gly Xaa Tyr Leu.
1               5               10
```

The compositions of the present invention of Formula 1 can be prepared by conventional synthetic and bioconjugate chemistry known in the art as described by Hermanson et al. [14], which is incorporated herein by reference in its entirety. The method for determining the extent of apoptosis of cells by fluorescence-activated cell sorter (FACS) analysis is also well known in the art [15]. Briefly, MDA-MB-231 cells are seeded in 12-well culture plates and grown to 80% confluency, followed by 72 h treatment with various concentrations of drugs in various combinations; untreated MDA-MB-231 cells are used as control. After the completion of treatment time cells are trypsinized, washed, and analyzed for dead or apoptotic cells by staining with propidium iodide (10 μg/ml) for 15 min, followed by flow cytometry (FACS Aria Ill, BD Biosciences, San Jose, CA, USA) at the Stanford FACS Facility. Data are analyzed by Flow Jo FACS analysis software (Tree Star, Ashland, OR, USA). GCV and CB1954 were purchased from Sigma-Aldrich (St Louis, MO, USA).

The compounds of the present invention represented by Formula I, commonly referred to as 'active pharmaceutical ingredient (API)' or 'drug substance' is typically formulated with pharmaceutically acceptable salts, buffers, diluents, carriers, adjuvants, preservatives, and excipients. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts include, but are not limited to acetate, adipate, citrate, tartarate, benzoate, phosphate, glutamate, gluconate, fumarate, maleate, succinate, oxalate, chloride, bromide, hydrochloride, sodium, potassium, calcium, magnesium, ammonium, and the like. The formulation technology for manufacture of the drug product is well-known in the art, and are described in "Remington, The Science and Practice of Pharmacy" [16], incorporated herein by reference in its entirety.

The final formulated product, commonly referred to as 'drug product,' may be administered enterally, parenterally, or topically. Enteral route includes oral, rectal, topical, buccal, ophthalmic, and vaginal administration. Parenteral route includes intravenous, intramuscular, intraperitoneal, intrasternal, and subcutaneous injection or infusion. The drug product may be delivered in solid, liquid, or vapor forms, or can be delivered through a catheter for local delivery at a target. Also, it may be administered alone or in combination with other drugs if medically necessary.

Formulations for oral administration include capsules (soft or hard), tablets, pills, powders, and granules. Such formulations may comprise the API along with at least one inert, pharmaceutically acceptable ingredients selected from the following: (a) buffering agents such as sodium citrate or dicalcium phosphate; (b) fillers or extenders such as starches, lactose, sucrose, glucose, mannitol, and silicic acid; (c) binders such as carboxymethylcellulose, alginates, gelatin, polyvinylpyrrolidone, sucrose and acacia; (d) humectants such as glycerol; (e) disintegrating agents such as agar-agar, calcium carbonate, potato or tapioca starch, alginic acid, certain silicates and sodium carbonate; (f) solution retarding agents such as paraffin; (g) absorption accelerators such as quaternary ammonium compounds; (h) wetting agents such as cetyl alcohol and glycerol monostearate; (i) absorbents such as kaolin and bentonite clay and (j) lubricants such as talc, calcium stearate, magnesium stearate, solid polyethylene glycols, sodium lauryl sulfate. and mixtures thereof; (k) coatings and shells such as enteric coatings, flavoring agents, and the like.

Liquid dosage forms for oral administration include pharmaceutically acceptable emulsions, solutions, suspensions, syrups and elixirs. In addition to the API, the liquid dosage forms may contain inert diluents, solubilizing agents, wetting agents, emulsifying and suspending agents, sweetening, flavoring, and perfuming agents used in the art.

Compositions suitable for parenteral injection may comprise physiologically acceptable, sterile aqueous or non-aqueous isotonic solutions, dispersions, suspensions or emulsions, and sterile powders for reconstitution into sterile injectable solutions or dispersions. The compositions may also optionally contain adjuvants such as preserving; wetting; emulsifying; dispensing, and antimicrobial agents. Examples of suitable carriers, diluents, solvents, vehicles, or adjuvants include, but are not limited to water; ethanol; polyols such as propyleneglycol, polyethyleneglycol, glycerol, and the like; vegetable oils such as cottonseed, groundnut, corn, germ, olive, castor and sesame oils, and the like; organic esters such as ethyl oleate and the like; phenol, parabens, sorbic acid, and the like.

Injectable formulations may also be suspensions that contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension. Alternatively, delayed absorption of a parenterally administered drug form is accomplished by dissolving or suspending the drug in an oil vehicle.

Injectable depot forms are made by forming microencapsulated matrices of the drug in biodegradable polymers. Depending upon the ratio of drug to polymer and the nature of the particular polymer employed, these compositions release the active ingredient(s) only, or preferentially, in a certain part of the intestinal tract, optionally, in a delayed manner. Thus, the rate of drug release and the site of delivery can be controlled. Examples of embedding compositions include, but are not limited to polylactide-polyglycolide poly(orthoesters), and poly(anhydrides), and waxes. The technology pertaining to controlled release formulations are described in "Design of Controlled Release Drug Delivery Systems," [17] incorporated herein by reference in its entirety.

Formulations for topical administration include powders, sprays, ointments and inhalants. These formulations include the API along with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art and are described in "Liposomes," [18], which is incorporated herein by reference in its entirety.

The compounds of the present invention can also be administered to a patient in the form of pharmaceutically acceptable 'prodrugs.' Prodrugs are generally used to enhance the bioavailability, solubility, in vivo stability, or any combination thereof of the API. They are typically prepared by linking the API covalently to a biodegradable functional group such as a phosphate that will be cleaved enzymatically or hydrolytically in blood, stomach, or GI tract to release the API. A detailed discussion of the prodrug technology is described in "Prodrugs: Design and Clinical Applications," [19] incorporated herein by reference.

The dosage levels of API in the drug product can be varied so as to achieve the desired therapeutic response for a particular patient. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; activity of the specific compound employed; the specific composition employed, age, body weight, general health, sex, diet of the patient; the time of administration, route of administration, and rate of excretion of the specific compound employed, and the duration of the treatment. The total daily dose of the compounds of this invention administered may range from about 0.0001 to about 1000 mg/kg/day. For purposes of oral administration, more preferable doses can be in the range from about 0.001 to about 5 mg/kg/day. If desired, the effective daily dose can be divided into multiple doses for optimal therapeutic effect.

Solid phase peptide synthesis. All the conjugates AMP-008 to AMP-016 were synthesized by Genemed Synthesis, San Antanio, TX, USA. Solid phase peptide synthesis (SPPS) was performed using a microwave-assisted peptide synthesizer (CEM) or in a standard manual reaction vessel under argon. Rink-amide MBHA resin and Wang resin were purchased from Sigma-Aldrich. DMF, DMSO, NMP, DCM, MeOH, ACN and DIEA were dried and distilled using standard protocols. The peptides were purified on a Merck Hitachi HPLC using a reverse-phase C8 semi-preparative column (Vydac) with a gradient of 5% to 60% acetonitrile in water (both containing 0.001% (v/v) trifluoroacetic acid). The 1H-NMR spectra were measured on 400 MHz or 600 MHz spectrometer (Bruker) and the 13C-NMR spectra were measured at a 100 MHz frequency using $CDCl_3$ as solvent.

The peptides identity was tested using MALDI-TOF Mass spectrometry on a PerSeptive Biosystems VoyagerDE PRO Biospectrometry workstation. The peptides purity was confirmed using analytical HPLC. Fmoc deprotection: The peptidyl-resin was treated twice with 20% piperidine in NMP for 30 minutes using microwave irradiation. The product was washed 4 times using NMP. HBTU/HOBt coupling of protected amino acids: Fmoc-protected amino acid (1.5 equiv), 1-hydroxybenztriazole hydrate (HOBt, 1.5 equiv), o-benzotriazole-1-yl-N,N,N,N-tetramethyluronium hexafluorophosphate (HBTU, 1.5 equiv) and diisopropyl-ethylamine (DIEA) (2 equiv) were dissolved in dry DMF. The solution was mixed with the resin-bound peptide and then irradiated in microwave for 5 minutes in the peptide synthesizer. The process was repeated twice and the resin was then washed with DMF, NMP and DCM. HBTU coupling of malonic acid: Malonic acid (1 equiv) was activated by adding HBTU (1.2 equiv) and DIEA (1.5 equiv) in DMF or DMSO. The mixture was stirred for 10 minutes at 0° C. and then added into a vessel containing pre-swollen resin-bound peptide in DMF or DMSO. The reaction was then allowed to continue for another 1 hr. The completion of the reaction was monitored by the Kaiser-ninhydrin and chloranil tests. Negative response in these color tests indicated the completion of the reaction. The resin was then washed thoroughly with DMF, DCM, Ethanol and diethyl ether.

Cleavage of the peptide from the resin: A solution (10 ml) of trifluoroacetic acid (TFA)/TDW/triisopropylsilane (TIS) (92:4.5:3.5) was cooled to 0° C. and incubated with 200 mg resin-bound peptide for 2 h. The cleaved peptide was precipitated with ice cold diethyl ether, the solution centrifuged and the peptide washed twice more with ether. Then minimum volume of ACN/TDW (3:2) was used to dissolve the crude peptide. The solution was lyophilized before purification in HPLC.

Optimization of the acetylation reaction conditions: The activation of malonic acid (1 equiv) by HBTU (1.2 equiv) was optimized in presence of different bases (1.5 equiv) in different organic solvents. The mixture was stirred for 10 minutes at 0° C. and then added to pre-swollen resin-bound peptide 4 in the different solvents. The reaction was then allowed to continue for another 1 hr. The completion of the reaction was monitored by the Kaiser-ninhydrin and chloranil tests.

The resin was then washed thoroughly with DMF, DCM, Ethanol and diethyl ether. A solution (10 ml) of trifluoroacetic acid (TFA)/TDW/triisopropylsilane (TIS) (92:4.5:3.5) was cooled to 0° C. and incubated with 200 mg resin-bound peptide 4 for 2 h. The cleaved peptide 30 was precipitated with ice cold diethyl ether, the solution centrifuged and the peptide washed twice more with ether. Then minimum volume of ACN/TDW (3:2) was used to dissolve the crude peptide and purified in HPLC. After optimization of bases and solvent system, it was concluded that DIPEA/Et3N in DMF/DMSO gave best yield in the shortest time.

The following examples illustrate specific embodiments and utilities of the invention, and are not meant to limit the invention. As would be apparent to skilled artisans, various modifications in the composition, operation, and method are possible, and are contemplated herein without departing from the concept and scope of the invention as defined in the claims.

Example 1

Synthesis of AAAPT Bioconjugate of Formula 1, wherein A is α-tocopherol; T is Val-Cit; L is —O(CH$_2$CH$_2$O)$_g$(CH$_2$)$_h$O—; and the Subscripts "g", and "h" are 1000, and 2 Respectively (AMP-001)

The general synthesis of cathepsin B cleavable peptide conjugation with pegylated apoptogen and/or other apoptogens is accomplished through Fmoc chemistry to protect N end of peptide with Boc and then couple it with tocopherol derivatives using DCC in DMF. This was further cleaved by TFA and purified using HPLC method. Cathepsin cleavable compounds have been synthesized by Genemed Synthesis using their proprietary peptide synthesis technology. In brief, peptides were synthesized using a microwave peptide synthesizer. The resin (containing 0.25 mmol of peptide anchors) was deprotected using piperidine resulting in the formation of the primary amine. The carboxylic acids of the Fmoc protected amino acids (1 mmol) were activated using COMU and conjugated to the primary amines of the growing peptide on the resin. The process of deprotection, activation and conjugation was repeated until the desired peptide was synthesized. Purification of the peptides was performed using a semi-preparative Kromasil C18, 5u column with a flow rate of 5.0 mL/min. HPLC solvents were 0.1% TFA acetonitrile (solvent A) and 0.1% TFA in water (solvent B). The initial gradient A:B, t=0, 10:90 and t=30 100% B. FIG. 3 shows a general synthesis procedure for all the compounds from AMP-001 to AMP-017.

Example 2

Synthesis of AAAPT Bioconjugate of Formula 1, Wherein A is α-Tocopherol; T is Val-Cit; L is —(CH$_2$)$_d$NH—; and the Subscript "d" is 3 (AMP-002)

Step 1. To a stirred solution of α-tocopherol 3 (2.5 g, 5.81 mmol) in dry DMF (15 mL) was added compound 2 (2.49 g, 10.46 mmol) followed by K$_2$CO$_3$ (2.3 g, 17.43 mmol) at RT under inert atmosphere. The resulting reaction mixture was gradually heated up to 65° C. and stirred for 16 h; progress of the reaction was monitored by TLC. The reaction mixture was diluted with ice-cold water (50 mL) and extracted with EtOAc (3×75 mL). The combined organic extracts were washed with water (75 mL), brine (50 mL), dried over anhydrous Na$_2$SO$_4$ and concentrated under reduced pressure. The crude material was purified by silica gel column chromatography (SiO2, 60-120 mesh) (eluent: 15% EtOAc/Hexane) to afford compound 4 (2.4 g, 4.08 mmol, 62%) as off white solid. $^1$H NMR (CDCl3): δ 3.75 (t, J=8.2 Hz, 2H)), 3.43 (t, J=8.2 Hz, 2H), 2.67 (t, J=7.2 Hz, 3H), 2.35 (t, J=7.2 Hz, 2H), 2.19-2.00 (m, 9H), 1.79-1.67 (m, 2H), 1.60-1.48 (m, 3H), 1.43-1.11 (m, 23H), 1.49 (s, 9H), 0.92-0.82 (m, 12H). LRMS (ESI): m/z 588 [M+H]$^+$.

Step 2: To a stirred solution of the Boc-protected compound in Step 1 (2.3 g, 3.91 mmol) in dry 1,4-dioxane (5 mL) was added 4 N 1,4-dioxane solution in HCl (2.3 mL) at 0° C. under inert atmosphere. The resulting reaction mixture was stirred at RT for 9 h. After completion of the reaction (by TLC), The resulting mixture was concentrated under reduced pressure to get the sticky syrup, after washing with ether (HPLC, 2×20 mL) to afford 5 as fine brown solid (1.2 g, 2.45 mmol, 62%). $^1$H NMR (CDCl3): δ 8.35 (bs, 3H), δ 3.35 (t, J=8.2 Hz, 2H)), 3.43 (t, J=8.2 Hz, 2H), 2.52 (t, J=7.2

Hz, 3H), 2.35 (t, J=7.2 Hz, 2H), 2.19-2.00 (m, 9H), 1.79-1.67 (m, 2H), 1.60-1.48 (m, 3H), 1.41-1.10 (m, 23H), 0.90-0.80 (m, 12H). LRMS (ESI): m/z 488 [M+H]$^+$.

Step 3. Briefly, the protected amino acids were mixed with precursor AMP-002 in peptide synthesizer with conditions of conjugating activating agents DCC. The product was chromatographed using solvent system chloroform and ethyl acetate to get the final product AMP-002 (yield 78%). The synthesis of cathepsin B cleavable peptide conjugation with apoptogen is accomplished through Fmoc chemistry to synthesize N end of peptide protected with Boc and then, couple it with tocopherol derivatives with DCC in DMF. This was further cleaved by TFA and purified using HPLC method. Cathepsin cleavable compounds have been synthesized by Genemed Synthesis using their proprietary peptide synthesis technology. In brief, peptides were synthesized using a microwave peptide synthesizer. The resin (containing 0.25 mmol of peptide anchors) was deprotected using piperidine resulting in the formation of the primary amine. The carboxylic acids of the Fmoc protected amino acids (1 mmol) were activated using COMU and conjugated to the primary amines of the growing peptide on the resin. The process of deprotection, activation and conjugation was repeated until the desired peptide was synthesized. Purification of the peptides was performed using a semi-preparative Kromasil C18, 5u column with a flow rate of 5.0 mL/min. HPLC solvents were 0.1% TFA acetonitrile (solvent A) and 0.1% TFA in water (solvent B). The initial gradient A:B, t=0, 10:90 and t=30 100% B.

Example 3

Synthesis of AAAPT Bioconjugate of Formula 1, Wherein A is α-Tocopherol; T is Val-Cit; L is —HN(CH$_2$)$_b$CO—; and the Subscript "b" is 3 (AMP-003)

Step 1. To a stirred solution of compound 4 (2.5 g, 5.81 mmol) in dry DMF (15 mL) was added compound 3 (3.1 g) followed by K$_2$CO$_3$ (2.76 g, 20.33 mmol) at ambient temperature under inert atmosphere. The resulting reaction mixture was gradually heated to 65° C. and stirred for 16 h. After completion of the reaction (as determined by TLC), the reaction mixture was diluted with ice-cold water (50 mL) and extracted with EtOAc (3×75 mL). The combined organic extracts were washed with water (75 mL), brine (50 mL), dried over anhydrous Na$_2$SO$_4$ and concentrated under reduced pressure. The crude material was purified by silica gel column chromatography (SiO2, 60-120 mesh) (eluent: 20% EtOAc/Hexane) to afford compound 5 (2.2 g, 3.57 mmol, 62%) as off white solid. $^1$H NMR (CDCl$_3$): δ 4.75 (bs, 1H), 3.30 (s, 2H), 2.66 (t, J=8.2 Hz, 2H), 2.60 (t, J=8.2 Hz, 2H), 2.83 (s, 3H), 2.00 (s, 6H), 1.86-1.72 (m, 3H), 1.59-1.20 (m, 34H), 0.90-0.82 (m, 12H). LRMS (ESI): m/z 616 [M+H]$^+$.

Step 2: To a stirred solution of compound-5 (2.1 g, 3.41 mmol) in dry 1,4-dioxane (5 mL) was added 4 N 1,4-dioxane solution in HCl (1.5 mL) at 0° C. under inert atmosphere. The resulting reaction mixture was stirred at RT for 9 h. After completion of the reaction (by TLC), The resulting mixture was concentrated under reduced pressure, to get the sticky syrup, after washing with ether (HPLC) to obtain compound 6 the fine brown solid (1.3 g, 2.52 mmol, 74%). $^1$H NMR (Varian, 400 MHz, CDCl$_3$): δ 8.10 (bs, 3H), 2.89 (t, J=7.2 Hz, 2H),), 2.79 (t, J=10 Hz, 2H), 2.57 (t, J=8.0 Hz, 2H), 2.01 (s, 3H), 1.91-1.89 (m, 9H), 1.75 (q, J=7.2 Hz, 2H), 1.40-1.33 (m, 3H), 1.29-1.02 (m, 23H), 0.84-0.80 (m, 12H). MS (ESI): m/z 516 [M+1]$^+$ HPLC: 91.68%.

Step 3. Briefly, the protected amino acids were mixed with precursor AMP-002 in peptide synthesizer with conditions of conjugating activating agents DCC. The product was chromatographed using solvent system chloroform and ethyl acetate to get the final product AMP-002 (yield 78%). The synthesis of cathepsin B cleavable peptide conjugation with apoptogen is accomplished through Fmoc chemistry to synthesize N end of peptide protected with Boc and then, couple it with tocopherol derivatives with DCC in DMF. This was further cleaved by TFA and purified using HPLC method. Cathepsin cleavable compounds have been synthesized by Genemed Synthesis using their proprietary peptide synthesis technology. In brief, peptides were synthesized using a microwave peptide synthesizer. The resin (containing 0.25 mmol of peptide anchors) was deprotected using piperidine resulting in the formation of the primary amine. The carboxylic acids of the Fmoc protected amino acids (1 mmol) were activated using COMU and conjugated to the primary amines of the growing peptide on the resin. The process of deprotection, activation and conjugation was repeated until the desired peptide was synthesized. Purification of the peptides was performed using a semi-preparative Kromasil C18, 5u column with a flow rate of 5.0 mL/min. HPLC solvents were 0.1% TFA acetonitrile (solvent A) and 0.1% TFA in water (solvent B). The initial gradient A:B, t=0, 10:90 and t=30 100% B.

Example 4

Synthesis of AAAPT Bioconjugate of Formula 1, Wherein A is α-Tocopherol; T is Val-Cit; L is —HN(CH$_2$)$_b$CO—; and the Subscript "b" is 3 (AMP-004)

The synthesis of Citrulline-valine conjugation with apoptogen is accomplished through Fmoc chemistry to synthesize carboxylic group protection and then, couple it with tocopherol derivatives with DCC in DMF. This was further cleaved by TFA and purified using HPLC method. Cathepsin cleavable compounds have been synthesized by Genemed Synthesis using their proprietary peptide synthesis technology. In brief, peptides were synthesized using a microwave peptide synthesizer. The resin (containing 0.25 mmol of peptide anchors) was deprotected using piperidine resulting in the formation of the primary amine. The carboxylic acids of the Fmoc protected amino acids (1 mmol) were activated using COMU and conjugated to the primary amines of the growing peptide on the resin. The process of deprotection, activation and conjugation was repeated until the desired peptide was synthesized. Purification of the peptides was performed using a semi-preparative Kromasil C18, 5u column with a flow rate of 5.0 mL/min. HPLC solvents were 0.1% TFA acetonitrile (solvent A) and 0.1% TFA in water (solvent B). The initial gradient A:B, t=0, 10:90 and t=30 100% B.

Example 5

Synthesis of AAAPT bioconjugate of Formula 1, (AMP-004), wherein A is human beta-defensin; T is MMP2 cleavable peptide, and said bioconjugate has SEQ ID NO: 003, wherein Xaa at position 1 is N-acetyl-glutamic acid (Ac-Glu) and at positions 6 and 8 are citrulline (Cit) and homophenylalanine (Hof) respectively, and wherein disulfide bonds are formed between each pair of cysteines 15 and 44, 22 and 37, and 27 and 45.

```
                                       SEQ ID NO: 003
Xaa Glu Glu Pro Xaa Gly Xaa Tyr Leu Asp His Tyr
1               5               10

Asn Cys Val Ser Ser Gly Gly Gln Cys Leu Tyr Ser Ala
    15              20              25

Cys Pro Ile Phe Thr Lys Ile Gln Gly Thr Cys Tyr Arg
            30              35

Gly Lys Ala Lys Cys Cys Lys
40              45
```

First, the MMP2-cleavable peptide sequence was synthesized using the procedure described earlier and the beginning amino acid E was capped with acetylation using acetic anhydride. The peptide acid was synthesized on the solid phase starting with commercially available Fmoc-Leu-Wang resin (0.40 g, 0.25 mmol, Advance Chemtech, Louisville, KY). The synthesis was done on an ABI 433A peptide synthesizer (Applied Biosystems, Foster City, CA) using standard Fmoc protocols. The completed peptide on resin was N-acetylated with acetic anhydride. The desired peptide was cleaved from the resin with 90% trifluoroacetic acid in water for 2 hours. After solvent removal, the peptide was dissolved in $H_2O:CH_3CN$ and conjugated to the commercially available hBD and freeze dried. Purification of the peptides was performed using a semi-preparative Kromasil C18, 5u column with a flow rate of 5.0 mL/min. HPLC solvents were 0.1% TFA acetonitrile (solvent A) and 0.1% TFA in water (solvent B). The initial gradient A:B, t=0, 10:90 and t=30 100% B.

Example 6

General Procedure for the Synthesis of Octreotate Cathepsin Cleavable Apoptogens (AMP-005, AMP-006 and AMP-007)

The synthesis of citrulline-valine conjugation with apoptogen is accomplished through Fmoc chemistry to synthesize carboxylic group protection and then, couple it with tocopherol derivatives with DCC in DMF. This was further cleaved by TFA and purified using HPLC method. The procedure was similar to the one used in the example 4. The valine-citrulline conjugate of apoptogen was further conjugated to the carboxylic group of commercially available Octreoscan using standard peptide coupling procedure.

Example 7

General Procedure for Cell Death Analysis by FACS

The method for determining the extent of apoptosis of cells by fluorescence-activated cell sorter (FACS) analysis is also well known in the art [15]. Briefly, MDA-MB-231 cells are seeded in 12-well culture plates and grown to 80% confluency, followed by 72 h treatment with various concentrations of drugs in various combinations; untreated MDA-MB-231 cells are used as control. After the completion of treatment time cells are trypsinized, washed, and analyzed for dead or apoptotic cells by staining with propidium iodide (10 μg/ml) for 15 min, followed by flow cytometry (FACS Aria 11, BD Biosciences, San Jose, CA, USA) at the Stanford FACS Facility. Data are analyzed by Flow Jo FACS analysis software (Tree Star, Ashland, OR, USA). GCV and CB1954 were purchased from Sigma-Aldrich (St Louis, MO, USA).

Example 8

General Procedure for Determining Synergy Between AMP Compounds and Doxorubicin

MDA-MB-231 tumor cells (ATCC) were cultured in 24-well plate for 18 hours. MMP2 cleavable AMP-008 was dissolved in culture medium and sonicated for 2 min each and repeated for 3 times. After the cells treated with different concentration of doxorubicin HCl (Bedford Lab, Bedford, OH), AMP compounds alone or combination of doxorubicin and AMP compounds were tested for 17 hrs incubation respectively, the cells were washed three times with PBS (pH 7.4) and incubated with Cy5.5 Annexin-V (BD Bioscience Pharmingen) according to the instructions of the manufacture. The cells were imaged using Nikon Eclipse TE-300 fluorescence microscope and counted under Ex/Em 620-680 nm nm/700-750 nm.

Example 9

Apoptosis Induction by AMP-001 & its Synergistic Effect with Doxorubicin (FIG. 4)

Concentration dependent treatment of AMP-001 on TNBC MDA-MB-231 cells showed cell death effect with IC-50 around 25-30 μM. AMP-001 was also treated with PC3 prostate cancer, 4T1 metastatic breast cancer, SKVO3 ovarian cancer, A549 lung cancer, GL 261 (Glioma), U 87 (Malignant Glioma) and TNBC patients cells using proliferation assays which showed inhibition of proliferation of cancer cells between the range 10-25 μM.

Example 10

Apoptosis Induction by AMP-001 and its Synergistic Effect with Doxorubicin (FIG. 5)

Concentration dependent treatment of AMP-001 on TNBC MDA-MB-231 cells showed cell death effect with IC-50 around 15 μM. AMP-002 was also treated with PC3 prostate cancer, 4T1 metastatic breast cancer, SKVO3 ovarian cancer, A549 lung cancer, GL 261 (Glioma), U 87 (Malignant Glioma) and TNBC Patients cells using proliferation assays an showed inhibition of proliferation of cancer cells between the range 5-20 μM. Pretreatment of same cells with AMP-001 for 6 hrs followed by 1 μM doxorubicin treatment resulted synergistic (not additive) effect of greater than 95% cell death compared to AMP-001 or doxorubicin alone. Synergistic effect was same when both were administered together. Treatment of AMP-001 on normal fibroblasts did not show significant cell death compared to cancer cells.

Example 11 (FIG. 6)

Apoptosis Induction by AMP-002 and its Synergistic Effect with Doxorubicin

Concentration dependent treatment of AMP-003 on TNBC MDA-MB-231 cells showed cell death effect with IC-50 around 5 μM. AMP-003 was also treated with PC3 prostate cancer, 4T1 metastatic breast cancer, SKVO3 ovarian cancer, A549 lung cancer, GL 261 (Glioma), U 87 (Malignant Glioma) and TNBC cells. using proliferation assays an showed inhibition of proliferation of cancer cells between the range 2-16 µM. Pretreatment of same cells with AMP-003 for 6 hrs followed by 1 µM doxorubicin treatment resulted synergistic (not additive) effect of greater than 75% cell death compared to AMP-002 or doxorubicin alone. Synergistic effect was same when both were administered together. Treatment of AMP-002 on normal fibroblasts did not show significant cell death compared to cancer cells (FIG. 7). Similarly, AMP-003 also showed dose dependent cell death with an $IC_{50}$ around 20-30 µM (FIG. 8).

Example 12

Apoptosis Induction by AMP-004 and its Synergistic Effect with Doxorubicin

Concentration dependent treatment of AMP-004 on TNBC MDA-MB-231 cells showed cell death effect with IC-50 around 5 µM (FIG. 9). Pretreatment of same cells with AMP-004 for 6 hrs followed by 1 µM doxorubicin treatment resulted synergistic (not additive) effect of greater than 80% cell death compared to AMP-003 or doxorubicin alone. Synergistic effect was same when both were administered together (FIG. 10). AMP-004 also showed similar synergistic effect another chemotherapy carboplatin (FIG. 11).

Example 13

Apoptosis Induction by AMP-005, AMP-006 and AMP-007

Concentration dependent treatment of AMP-005, AMP-006 and AMP-007 on TNBC MDA-MB-231 cells showed cell death with $IC_{50}$ around 12, 18 and 23 µM respectively (FIG. 12-14).

Example 14 (FIG. 15)

Tissue Accumulation and Tumor Growth Inhibitory Activity of Dose Dependent AMP-001 "In Vivo" MDA-MB-231-Luc Xenograft Model The anti-tumorogenic potential of AMP-001 was tested using a limited number of female Nu/Nu mice (4-6 weeks old) which were innoculated in the mammary fat pad with $5 \times 10^6$ MDA-MB-231 cells stably expressing firefly luciferase. Tumors were allowed to reach 150-200 mm³ before I.P. administration of AMP-001. The treatment schedule for this experiment was AMP-001 monotherapy at low (100 µM/kg) and high (500 µM/kg) dose×3 days×2 weeks. Tumor response was monitored by bioluminescence (IVIS 200, Perkin Elmer). No toxicity was detected as far as significant weight loss, decreased mobility or labored breathing is concerned. The light intensities emitted from regions of interest were expressed as total flux (photons/second). The data clearly establish that AMP-001 regresses tumor at a reasonable dose 51 mg/Kg while, not showed any toxicity up to 1000 mg/kg. The mice were monitored for behavioral changes along with weigh loss for 41 days. FIG. 15A shows a significant reduction in the bioluminescent signal correlated to tumor volume plotted as a percentage of tumor growth normalized at day 1 of injection (FIG. 15B, p<0.05) compared to untreated control. The V curve confirms tumor regression for dose 2.

Example 16 (FIG. 16)

Tumor Regression Study with AMP-001 in MDA-MB-231 Triple Negative Breast Cancer Animal Model Efficacy and toxicity in vivo are the main criteria for a successful clinical translation from in vitro. Nude mice with age group of 4 to 5 weeks were purchased from Charles River animal supplier (Charles River Laboratories, Wilmington, MA), and put in to Stanford University animal facility for quarantine. To make sub-cutaneous tumor model, mice were implanted with 10 millions of MDA-MB-231 cells stably expressing FLuc-EGFP fusion protein, on either flank regions of hind limps. Animals were maintained in sterile disposable cages until the tumor size reach 50 to 100 mm³. Nude mice were divided into 3 groups comprising N=8 animals in each group, and 1 group with 3 animals. Group with 3 animals were treated with vehicle control (250 µL physiological saline containing 10% PEG400), and other 3 groups with N=8 in each group were treated with 50, 100 and 200 mg/Kg BW in 250 µL physiological saline containing 10% PEG400. AMP-001 was administered by intraperitoneal route for 7 times with a interval of 48 h. For optical imaging, animals were intraperitoneally injected with 3 mg of D-Luciferin in 100 µl PBS, 5 to 10 minutes before signal acquisition. All mice were imaged with a cooled CCD camera (Spectral Lago; Spectral Instruments Imaging, Tucson, AZ), and photons emitted were collected and integrated for a period of 15 seconds for 20 acquisitions for FLuc. Images were analyzed by Spectral Instruments Imaging Software (Spectral Instruments Imaging, Tucson, AZ). To quantify the number of emitted photons, regions of interest (ROI) were drawn over the area of the implanted cells, and the maximum photons per second per square centimeter per steradian (p/sec/cm²/sr) were recorded. Tumor volume and animals weights were recorded after every imaging session. After Imaging, animals were euthanized and tissues samples from tumor, kidney, liver, pancreas, heart, and lung were fixed for histological and toxicological examinations. Result: No toxicity was detected as far as significant weight loss, decreased mobility, grooming behavior or labored breathing are concerned. FIG. 16 A shows a significant reduction in the bioluminescent signal correlated to tumor volume plotted as a percentage of tumor growth normalized at day 1 of injection (FIG. 16 B, p<0.05) compared to untreated control. The classic V curve confirms tumor regression for dose 200 mg/Kg BW.

Example 17 (FIG. 17)

Ex Vivo Histological Studies on Tissues of Mice Post-Treated with AMP-001

Animals from all groups were euthanized and tissue samples were collected. After Imaging, animals were euthanized and tissues samples from kidney, liver, heart, spleen, and tumor were fixed with OCT fixative for histological and toxicological examinations. H&E stained and Ki67 stained tissue sections did not show any toxicological abnormalities. Tumor tissue section from animals treated with AMP-002, 2 dose 2 showed marked tissue damage.

Example 18 (FIG. 18)

Assessment of Cardiotoxicity of AMP-001 and AMP-002 Conjugate. Adult Human Heart Cell Generation and Cell Culture In brief, the adult human heart cell line was created by reprogramming an adult human fibroblast cell line by retroviral expression of the reprogramming factors sox7, oct4, nanog, and lin28 using MMLV viral constructs. This line was used to generate stem-cell clones which were engineered to exhibit blasticidin resistance by inserting the coding region of the BSD gene encoding Blasticidin S Deaminase from *Aspergillus terreus* in-frame downstream of the last exon of the native myosin heavy chain 6 (MYH6) gene coding region through homologous recombination. Cardiomyocytes were derived from this engineered stem cell clone line as follows. Stem cell aggregates were formed from single cells and cultured in suspension in medium containing zebrafish bFGF (basic fibroblast growth factor) and fetal bovine serum. Upon observation of beating cardiac aggregates, cultures were subjected to blasticidin selection at 25 ug/ml to enrich the cardiomyocyte population. Cardiomyocyte aggregate cultures were maintained in Dulbecco's modified Eagle's medium (DMEM) containing 10% fetal bovine serum during cardiomyocyte selection through the duration of the culture prior to cryopreservation. At 30 to 32 days of culture the enriched, stem cell-derived cardiomyocytes were subjected to enzymatic dissociation using 0.5% trypsin to obtain single cell suspensions of purified cardiomyocytes, which were >98% cardiac troponin-T (cTNT) positive. These cells (iCell® Cardiomyocytes) were cryopreserved and stored in liquid nitrogen before delivery to Ionic Transport Assays from Cellular Dynamics International, Madison, WI.

For this study, single vials containing≈4.5×10$^6$ cardiomyocytes were thawed by immersing the frozen cryo-vial in a 37° C. water bath, transferring thawed cardiomyocytes into a 50 ml tube and diluting them with room temperature plating medium (iCell® Cardiomyocyte Plating Medium (iCPM), Cellular Dynamics International).

Cells were plated into 6 well plates that percolated with 0.1% gelatin. This was defined as culture day 1 for the purpose of this study. Cell plating media was changed at day 3 to cell maintenance media and cell maintenance media subsequently was changed three times a week. Day 5-7 cells were re-suspended with trypsin and re-plated as desired density (>10,000) at 96 well plate which percolated with 0.1% gelatin). Results: The results show the comparison of IC-50 values for AMP-001 compared to doxorubicin and standard Sorafinib. The higher $IC_{50}$ value for AMP-001 in cardiomyocytes (>250 μM) compared to doxorubicin (9.6 μM) clearly demonstrates better safety profile for AMP-001. Photomicrographs of the morphology of cardiomyocytes showed that either 50 μM AMP-001 or 100 μM AMP-002 retained viability while, 10 μM doxorubicin resulted in cell death.

Example 19 (FIG. 19)

Synergy of AMP-001 with Doxorubicin in Gastric Cancer Animal Model In Vivo

Six-week-old athymic BALB/cA nu/nu female mice were purchased from Weitonglihua Laboratory (Beijing, China) and maintained in an Animal Biosafety Level 3 Laboratory at the Animal Experimental Center of Wuhan University. All animal experiments were performed according to the Wuhan University Animal Care Facility and National Institutes of Health guidelines. Approximately 5×10$^6$ MGC-803 cells were harvested and suspended in 200 μl of PBS and Matrigel (BD Bio-science) (1:1), and injected subcutaneously into the right flank of each mouse. After two weeks xenotransplantation, mice were respectively randomized into four groups and treated as follow: VCPA (same as AMP-001, 10 mg/kg i.p. every other day for 3 weeks), DOX (1 mg·kg i.p. every other day for 3 weeks), their combination, or saline as untreated vehicle. The size of subcutaneous tumors and mice weight were recorded every two days. The tumor volume (V) was calculated according to the formula V=0.5×I×w$^2$, where I is the greatest diameter and w is the diameter at the point perpendicular to I. At the end of treatment, mice were sacrificed, and the tumors were removed and used for immunohistochemical staining. Result: The extent of tumor regression for either doxorubicin or for VCPA (AMP-001) is reasonable. However, a combination of AMP-001 and doxorubicin showed a significant synergistic tumor regression.

Example 20 (FIG. 20)

Suppression of Growth of Human Gastric Cancer Cells, Apoptosis and $IC_{50}$ Drift of Doxorubicin in Combination with AMP-001 (VCPA)

(A) AMP-001 (VCPA) suppresses the growth of human gastric cancer cells (SGC-7901 and MGC-803) (B) AMP-001 (VCPA) induces apoptosis in human gastric cancer cells SGC-7901 and MGC-803, (C) $IC_{50}$ drift of DOX only or AMP-001 (VCPA)/DOX combination treatment, in gastric cancer cells. Results: (A) Dose dependent AMP-001 reduced the growth of gastric cancer cells back to the base level, (B) induced cell death 48% in SGC-7901 while, it induced 58% in MGC-803 gastric cancer cells (C) $IC_{50}$ of the combination of doxorubicin and AMP-001 is reduced from 0.436 for doxorubicin to 0.065 (almost 10 times less) in SGC-7901 cells and from 1.076 to 0.111 in MGC-803.

Example 21 (FIG. 21)

Measuring $IC_{50}$ in Human Gastric Cancer Cell Lines $IC_{50}$ of AMP-001 (VCPA) in gastric cancer cell lines. Result: $IC_{50}$ of AMP-001 (VCPA) is around 14.25 μM for SGC-7901 and 16.91 μM for MGC-803.

Example 22 (FIG. 22)

Inhibition of Mammosphere Formation by AMP-001 in CSC Enriched Cancer Cells

Inhibition of mammosphere formation by AMP-001 in cancer stem cells (CSCs) in (MCF-10A) breast cells overexpressed with Src oncogene and b) in TMD-231 cells. Result: Controls showed 120-140 mammosphers/2000 MCF-10A-ER-Src Cells (Views 1 & 2 in Fig). B. Post AMP-001 treatment (5 μM/10 μM) reduced the mammosphers by 15-20 times (7-9/2000 cells) C: Control in TMD-231, 450-500 mammosphers/2000. D-E: Post AMP-001 Treatment: (5 μM/10 μM): Mammosphere reduction: 18-20 times (25-27/2000 cells). Conclusion: AMP-001 Inhibited mammosphere formation, A first step for the survival of CSCs.

Example 23 (FIG. 23)

AMP-001 radiosensitizes MDA-MB-231 Tumor cells. Result: Based on the chemosensitization of the basic core AMP-001, radiosensitization of MDA-MB-231 cells by AMP-001 was assessed through clonogenic assay. The cells were plated across different groups for each radiation dose (0-8 Gy) with or without AMP-001 (30 PM). TNBC cells were seeded in six-well plates and irradiated with 6 MV x-ray from a linear accelerator (Varian Medical Systems, Palo Alto, CA, USA) After 20 hours incubation, medium was replaced with drug-free, FBS-containing medium, and cells were incubated for 9 days to allow colony formation. Colonies were fixed in methanol and stained with 0.5% crystal violet, and the surviving fraction was calculated. FIG. 23 shows significant lowering of surviving fractions of TNBC cells at 8 Gy for combination of AMP-001 and radiation (p<0.005) compared to radiation alone.

REFERENCES

1. Kristina Viktorsson, Rolf Lewensohn and Boris Zhivotovsky. Apoptotic Pathways and Therapy Resistance in Human Malignancies. Adv Cancer Res. 2005, 94, 143-96.
2. Meyn R E, Stephens L C, Hunter N R, et al: Apoptosis in murine tumors treated with chemotherapy agents. *Anti-Cancer Drugs* 1995, 6, 443-450.
3. H. DarÃou. A Lu, M. Toyoda, T. Tenjo, and N. Tanigawa. Inhibition of Apoptosis by Survivin Predicts Shorter Survival Rates in Colorectal Cancer. *Cancer Research* 1998, 58, 5071-5074.
4. Y. Soini, P. Paakko, and V-P. Lehto, Histopathological Evaluation of Apoptosis in Cancer. *American Journal of Pathology* 1998, 153, 1041-53.
5. Mark P Mattson. Apoptosis in neurodegenerative disorders. *Nature* 2000, 120-129.
6. Herold Yan Ouyang, Marla J. Keller, Robert I. Lehrer and Betsy C. Ehsan Hazrati, Benjamin Galen, Wuyuan Lu, Wei Wang, Infection Human α- and β-Defensins Block Multiple Steps in Herpes Simplex Virus. *J. Immunol.* 2006, 177, 8658-8666.
7. Masao Saitoh, Hideki Nishitoh, Makiko Fujii, Kohsuke Takeda, Kei Tobiume, Yasuhiro Sawada, Masahiro Kawabata, Kohei Miyazono and Hidenori Ichijo, Mammalian thioredoxin is a direct inhibitor of apoptosis signal-regulating kinase (ASK) 1. *The EMBO Journal* 1998, 17, 2596-2606.
8. Gordon McLennan, Stacy L. Bennett, Shenghong Ju, Andriy Babsky, Navin Bansal, Michelle L. Shorten, Seth Levitin, Laurent Bonnac, Krystoff W. Panciewicz, Hiramagular N. Jayaram. Tumor Response and Apoptosis of N1-S1 Rodent Hepatomas in Response to Intra-arterial and Intravenous Benzamide Riboside. *Cardiovasc. Interven. Radiol.* 2012, 35(3):645-52.
9. Chunrong Yu, Bret B. Friday, Jin-Ping Lai, et al. Cytotoxic synergy between the multikinase inhibitor sorafenib and the proteosome inhibitor bortezomib in vitro: induction of apoptosis through Akt and c-Jun $NH_2$-terminal kinase pathways, *Mol. Cancer Ther.* 2006, 5, 2378-2387.
10. G. M. Ledda-Columbano, P. Coni, G. Faa, G. Manenti, t and A. Columbano, Rapid Induction of Apoptosis in Rat Liver by Cycloheximide. *Am. J. Pathol* 1992, 140, 545-549.
11. Pei-Ching Hsiao, Yi-Hsien Hsieh, Jyh-Ming Chow, Shun-Fa Yang, Michael Hsiao, Kuo-Tai Hua, Chien-Huang Lin, Hui-Yu Chen, and Ming-Hsien Chien. Hispolon Induces Apoptosis through JNK1/2-Mediated Activation of a Caspase-8, -9, and -3-Dependent Pathway in Acute Myeloid Leukemia (AML) Cells and Inhibits AML Xenograft Tumor Growth in Vivo. *J. Agri. Chem.* 2013, 61, 10063-10073.
12. G. M. Dubowchik, R. A. Firestone, L. Padilla, D. Willner, S. J. Hofstead, K. Mosure, J. O. Knipe, S. J. Lasch, P. A. Trail, Cathepsin B-labile dipeptide linkers for lysosomal release of doxorubicin from internalizing immunoconjugates: model studies of enzymatic drug release and antigen-specific in vitro anticancer activity. *Bioconjug. Chem.* 2002, 13, 855-869.
13. Schulthess F T, Katz S, Ardestani A, Kawahira H, Georgia S, Bosco D, Bhushan A, Maedler K. Deletion of the mitochondrial flavoprotein apoptosis inducing factor (AIF) induces beta-cell apoptosis and impairs beta-cell mass. PLoS One 2009, 4, e4394.
14. Bioconjugate Techniques; Greg T. Hermanson, ISBN: 978-0-12-370501-3, 2013.
15. *Flow Cytometry in Clinical Diagnosis*, v4, (Carey, McCoy, and Keren, Eds.), ASCP Press, 2007. ISBN 0-89189-548-5.
16. "Pharmaceutical Manufacturing. In *Remington: The Science and Practice of Pharmacy*. Lippincott Williams & Wilkins, Philadelphia, 2005, 691-1058.
17. "Li, X. *Design of Controlled Release Drug Delivery Systems*. McGraw-Hill, New York, 2006.
18. Rautio, J. et al. *Nature Reviews Drug Discovery* 2008, 7, 255-270.

I claim:

1. A method for enhancing the efficacy of tumor chemotherapy, radiation therapy or radionuclide therapy agent through a priori activation of apoptosis pathways of tumors, 'AAAPT', said method comprising administration to a patient with a tumor (a) a bioconjugate of Formula 3,

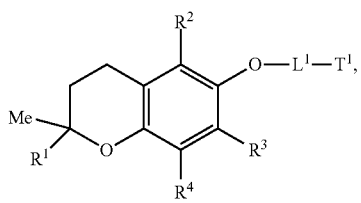

Formula 3 and (b) a chemotherapeutic agent, a radiation therapy agent, or a radionuclide therapy agent;

wherein

T is a somatostatin receptor binding agent or a cathepsin B binding agent;

L is $-NH(CH_2)_bCO-$, $-OC(CH_2)_cNH-$, $-(CH_2)_dNH-$, $-HN(CH_2)_e-$, $-O(CH_2)_f(CH_2CH_2O)_g(CH_2)_hO-$, $-HN(CH_2)_i(CH_2CH_2O)_j(CH_2)_kNH-$ or $-(AA)_n-$, wherein AA is a dipeptide;

subscripts 'b', 'c', 'd' and 'e' independently vary from 1-10;

subscripts 'f', 'g', 'h', 'i', 'j' and 'k' are independently vary from 1-100;

subscript 'n' varies from 1 to 10;

R1 is $C_1$-$C_{20}$ straight or branched alkyl, $C_3$-$C_{20}$ cycloalkyl, $C_1$-$C_{20}$ straight or branched alkenyl, $C_5$-$C_{10}$ alkyl, or $C_5$-$C_{20}$ arylalkyl;

each of R2, R3 and R4 is independently hydrogen or methyl;

said chemotherapy agent comprises doxorubicin, Bevacizumab, epirubicin, paclitaxel, docetaxel, 5-fluorouracil, cyclophosphamide, cisplatin, carboplatin, vinorelbine, capecitabine, liposomal doxorubicin, gemcitabine, ixabepilone, albumin-bound paclitaxel, eribulin, irinotecan, etoposide, vinblastine, tamoxifen, methotrexate or pemetrexed;

said radiation therapy is external beam radiation; and said radionuclide therapy agent comprises $^{123}I$, $^{125}I$, $^{131}I$, $^{186/188}Re$, $^{111}In$, $^{177}Lu$, $^{153}Sm$, $^{89}Sr$, $^{90}Y$, $^{201}Pb$, $^{32}P$, $^{198}Au$, $^{165}Dy$, $^{80m}Br$, $^{67}Cu$ or $^{117}Sn$.

2. The method of claim 1, wherein the cathepsin B binding agent is valine-citrulline;

L is $-O(CH_2)_f(CH_2CH_2O)_g(CH_2)_hO-$;

subscript 'g' varies from 10 to 20;

subscript 'h' is 2;

$R^1$ is $C_{16}$ branched alkyl; and each of $R^2$, $R^3$, or $R^4$ is methyl;

the chemotherapy agent is doxorubicin, Bevacizumab, paclitaxel, docetaxel, cyclophosphamide, cisplatin, carboplatin, gemcitabine, ixabepilone, eribulin, irinotecan, etoposide, vinblastine, or pemetrexed; and the radionuclide therapy agent is $^{186/188}$Re, $^{177}$Lu, $^{153}$Sm, $^{90}$Y, $^{201}$Pb, or $^{198}$Au.

3. The method of claim 1, wherein the cathepsin B binding agent is valine-citrulline;

L is —(CH$_2$)$_d$NH—;

subscript "d" is 3;

$R^1$ is C$_{16}$ branched alkyl;

each of $R^2$, $R^3$, or $R^4$ is methyl;

the chemotherapy agent is doxorubicin, Bevacizumab, paclitaxel, docetaxel, cyclophosphamide, cisplatin, carboplatin, gemcitabine, ixabepilone, eribulin, irinotecan, etoposide, vinblastine, or pemetrexed; and the radionuclide therapy agent is $^{186/188}$Re, $^{177}$Lu, $^{153}$Sm, $^{90}$Y, $^{201}$Pb, or $^{198}$Au.

4. The method of claim 1, wherein the cathepsin B binding agent is valine-citrulline;

L is —OC(CH$_2$)$_c$NH—; subscript "c" is 3;

$R^1$ is C$_{16}$ branched alkyl;

each of $R^2$, $R^3$, or $R^4$ is methyl;

the chemotherapy agent is doxorubicin, Bevacizumab, paclitaxel, docetaxel, cyclophosphamide, cisplatin, carboplatin, gemcitabine, ixabepilone, eribulin, irinotecan, etoposide, vinblastine, or pemetrexed; and the radionuclide therapy agent is $^{186/188}$Re, $^{177}$Lu, $^{153}$Sm, $^{90}$Y, $^{201}$Pb, or $^{198}$Au.

5. The method of claim 1, wherein the cathepsin B binding agent is valine-citrulline;

L is —HN(CH$_2$)$_b$CO—; subscript "b" is 3;

$R^1$ is C$_{16}$ branched alkyl;

each of $R^2$, $R^3$, or $R^4$ is methyl;

the chemotherapy agent is doxorubicin, liposomal doxorubicin, cisplatin, carboplatin, paclitaxel, albumin-bound paclitaxel, or docetaxel; and the radionuclide therapy agent is $^{186/188}$Re, $^{177}$Lu, $^{153}$Sm, $^{90}$Y, $^{201}$Pb, or $^{198}$Au.

6. The method of claim 1, wherein the somatostatin receptor binding agent is octreotate;

L is -(AA)$_n$-;

subscript 'n' is 2;

AA is the dipeptide valine-citrulline;

$R^1$ is C$_{16}$ branched alkyl; and each of $R^2$, $R^3$, or $R^4$ is methyl;

the chemotherapy agent is doxorubicin, Bevacizumab, paclitaxel, docetaxel, cyclophosphamide, cisplatin, carboplatin, gemcitabine, ixabepilone, eribulin, irinotecan, etoposide, vinblastine, or pemetrexed; and the radionuclide therapy agent is $^{186/188}$Re, $^{177}$Lu, $^{153}$Sm, $^{90}$Y, $^{201}$Pb, or $^{198}$Au.

* * * * *